US012766213B2

(12) United States Patent
Hale

(10) Patent No.: US 12,766,213 B2
(45) Date of Patent: Oct. 20, 2026

(54) SYSTEM, APPARATUS, AND METHOD FOR REMOVING PATHOGENS FROM A DENTAL OPERATORY

(71) Applicant: Robert G. Hale, Woodland Hills, CA (US)

(72) Inventor: Robert G. Hale, Woodland Hills, CA (US)

( * ) Notice: Subject to any disclaimer, the term of this patent is extended or adjusted under 35 U.S.C. 154(b) by 880 days.

(21) Appl. No.: 17/999,466

(22) PCT Filed: May 28, 2021

(86) PCT No.: PCT/US2021/034977

§ 371 (c)(1),
(2) Date: Nov. 21, 2022

(87) PCT Pub. No.: WO2021/243279

PCT Pub. Date: Dec. 2, 2021

(65) Prior Publication Data

US 2023/0201404 A1 Jun. 29, 2023

Related U.S. Application Data

(60) Provisional application No. 63/073,662, filed on Sep. 2, 2020, provisional application No. 63/031,351, filed on May 28, 2020.

(51) Int. Cl.
*A61L 9/14* (2006.01)

(52) U.S. Cl.
CPC .................................... *A61L 9/145* (2013.01)

(58) Field of Classification Search
CPC ........................................................ A61L 9/14
See application file for complete search history.

(56) References Cited

U.S. PATENT DOCUMENTS 3,537,447 A 11/1970 Gauthier et al.
3,881,477 A 5/1975 Von Otto
(Continued)

FOREIGN PATENT DOCUMENTS

CN 204428374 U 7/2015
GB 1 475 078 6/1977
(Continued)

OTHER PUBLICATIONS

Extended European Search Report issued Jun. 21, 2024, in corresponding European Patent Application No. 21814590.2, 11 pages.
(Continued)

*Primary Examiner* — Donald R Spamer
(74) *Attorney, Agent, or Firm* — Oblon, McClelland, Maier & Neustadt, L.L.P.

(57) ABSTRACT

The present disclosure relates to a device for generating an air containment envelope for the mitigation of pathogen transmission. In particular, the present disclosure relates to a system for removing pathogens from a dental operatory, comprising a manifold in fluid connection with a fluid source, the manifold including a plurality of apertures for directing a fluid stream, a fluid pump for pressurizing a fluid within the fluid source, and processing circuitry configured to instruct the fluid pump to pressurize the fluid, and instruct the fluid pump to pump the pressurized fluid to the manifold such that the directed fluid stream generates a fluid shield relative to an object.

20 Claims, 30 Drawing Sheets

(56) References Cited

U.S. PATENT DOCUMENTS

| | | | | |
|---|---|---|---|---|
| 2004/0005252 | A1 | 1/2004 | Siess | |
| 2006/0243902 | A1 * | 11/2006 | Altes Royo | G01N 1/24 250/288 |
| 2008/0188170 | A1 | 8/2008 | Della Valle et al. | |
| 2010/0280436 | A1 | 11/2010 | Self et al. | |
| 2014/0349564 | A1 * | 11/2014 | Lamothe | F24F 8/10 454/188 |
| 2016/0018117 | A1 | 1/2016 | Sekiguchi et al. | |
| 2017/0003015 | A1 | 1/2017 | Schreiber | |
| 2018/0153637 | A1 | 6/2018 | Al-Shawi et al. | |
| 2019/0117331 | A1 | 4/2019 | Self et al. | |
| 2019/0234645 | A1 * | 8/2019 | Haar | F24F 7/003 |
| 2022/0063814 | A1 * | 3/2022 | Vandyke | F24F 9/00 |

FOREIGN PATENT DOCUMENTS

| | | | |
|---|---|---|---|
| GB | 1 531 514 | A | 11/1978 |
| JP | 60-18164 | A | 1/1985 |
| WO | WO 2019/227828 | A1 | 12/2019 |

OTHER PUBLICATIONS

International Search Report & Written Opinion issued Sep. 24, 2021 in PCT/US2021/034977 filed on May 28, 2021, 9 pages.

* cited by examiner

SYSTEM, APPARATUS, AND METHOD FOR REMOVING PATHOGENS FROM A DENTAL OPERATORY

CROSS-REFERENCE TO RELATED APPLICATIONS

The present application claims priority to U.S. Provisional Application No. 63/031,351, filed May 28, 2020, the teaching of which is incorporated by reference herein in its entirety for all purposes.

BACKGROUND

Field of the Disclosure

The present disclosure relates to a system and method for reducing the incidence of pathogen transmission between patient and doctor during dental surgery.

Description of the Related Art

Despite compliance of the surgeon and surgical staff with rigorous hygiene principles and infection control protocols, airflow in an operating room can affect infection rates by allowing certain bacteria to get to a wound or other access site in a patient. The bacteria can be blown into the wound from health care providers' (surgeon, nurses, anesthesiologist, technicians, etc.) skin, hair, clothing, or hands. In addition, bacteria or other pathogens can contaminate an open wound, for example, when entrained in air entering the operating room while a door to the operating room is open. Bacteria or other pathogens from a prior surgical procedure or cleaning exercise by cleaning staff may become airborne. As a result, and in an attempt to mitigate and/or prevent such contamination, laminar flow of HEPA-filtered air has also been employed in the operating room to reduce scatter of bacteria into a surgical wound.

Conventional laminar flow systems operate by drawing ambient air, under negative pressure, into a laminar flow unit. This air first passes through a pre-filter which traps the larger size dust and dirt particles. A blower in the unit then directs this pre-filtered air, now under positive pressure, through a conventionally-known 99.97% efficient HEPA filter to generate sterile, unidirectional ultraclean air. The HEPA filter can remove particles down to a size of 0.300 microns. Bacteria range in size from 0.3 μm to 5 μm. Viruses range in size from 0.250 μm to 0.500 μm. Fortunately, viruses circulating in air are part of droplet nuclei measuring 1 μm to 5 μm in size.

Understanding the deficiencies of operating theaters in preventing the potential spread of some pathogens, including viruses, it can be appreciated that the ability to perform surgical procedures is greatly hampered by the emergence of a novel coronavirus. Such viruses can have a particular impact on dental surgeries that are most often performed in a small room (i.e., ~80 square feet) that may be an enclosed, a semi-enclosed, or an open bay with little preparation for airborne pathogens. Often, these rooms have half height walls for privacy and are placed within a commercial office setting or converted home setting that includes particle board drop ceilings, standard office finish materials, and commercial office-grade above-ceiling mounted heating and cooling, among others. The typical dental operatory equipment includes a dental patient chair, stool(s), a dental unit for powered instruments and fluid management devices, and an overhead light source. Cutting or drilling the dentition of a patient is performed by a dentist using a hand-held high speed pneumatic air turbine or electric drill having variable rotational speeds of up to and over 200,000 rpm. In order to manage heat generation and debris, as hard tissues or hard prosthetic materials of diseased or failed dentition are surgically cut and shaped at high drilling speeds, an irrigation fluid such as air or water may be sprayed directed from a jet orifice at the head of the air turbine or drill, and/or a separate three-way air/water hand-held syringe device, and directed by a dental assistant who also suctions the oral cavity free of irrigation fluid and excess saliva with a high volume suction device held by the opposite hand.

During an operation, however, and as a result of high speed drilling and use of irrigation fluids for debris control and thermal management, certain matter may become aerosolized, referred to herein by the general term of 'bioaerosol'. Considered in view of airborne pathogens, including novel coronaviruses, the relatively unregulated setting of a dental operatory confronts a unique challenge. Novel coronaviruses, for instance, are highly contagious airborne pathogens, with an estimated hospitalization rate of 20% of those infected, and deadly to vulnerable populations. As a result, in times of pandemic-levels of airborne pathogens, dental operations may be all but ceased, especially aerosolizing procedures, as efforts to prevent transmission of disease are the focus.

To this end, dentistry is considered by Centers for Disease Control and Prevention and Occupational Safety and Health Administration to be a very high risk occupation as it is believed most dental procedures aerosolize saliva which could contain SARS-CoV-2, a novel coronavirus. This determination is based on the assumption that drilling or polishing teeth under irrigation fluids can spread pathogens into the ambient air. In reality, however, this phenomenon has not been scientifically evaluated. Regardless, dentistry, now faced with a pandemic of epic proportions, must adapt to new technologies never developed. Even assuming the advent of an effective vaccine for COVID-19, recent world experiences of SARS-1, MERS, and SARS-2 will compel healthcare facilities to upgrade engineering/environmental controls and PPE to mitigate the onslaught of airborne pathogen threats.

With this in mind, the present disclosure addresses the need to evaluate airborne pathogens in dental operating rooms and the need to develop new technologies to mitigate the spread of disease.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to removing pathogens from an ambient environment of a dental operatory.

According to an embodiment, the present disclosure further relates to a system for removing pathogens from a dental operatory, comprising a manifold in fluid connection with a fluid source, the manifold including a plurality of apertures for directing a fluid stream, a fluid pump for pressurizing a fluid within the fluid source, and processing circuitry configured to instruct the fluid pump to pressurize the fluid, and instruct the fluid pump to pump the pressurized fluid to the manifold such that the directed fluid stream generates a fluid shield relative to an object.

According to an embodiment, the present disclosure further relates to an apparatus for removing pathogens from a dental operatory, comprising a manifold in fluid connection with a fluid source, the manifold including a plurality of apertures for directing a fluid stream, a fluid pump for pressurizing a fluid within the fluid source, and processing circuitry configured to instruct the fluid pump to pressurize the fluid, and instruct the fluid pump to pump the pressurized fluid to the manifold such that the directed fluid stream generates a fluid shield relative to an object.

According to an embodiment, the present disclosure further relates to a system for removing pathogens, comprising a manifold in fluid connection with a fluid source, the manifold including a plurality of apertures for directing a fluid stream, a fluid pump for pressurizing a fluid within the fluid source, and processing circuitry configured to instruct the fluid pump to pressurize the fluid, and instruct the fluid pump to pump the pressurized fluid to the manifold such that the directed fluid stream generates a fluid shield relative to an object.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 2 is an illustration of an air control device implemented within a dental operatory, according to an exemplary embodiment of the present disclosure;

DETAILED DESCRIPTION

Figure 1:
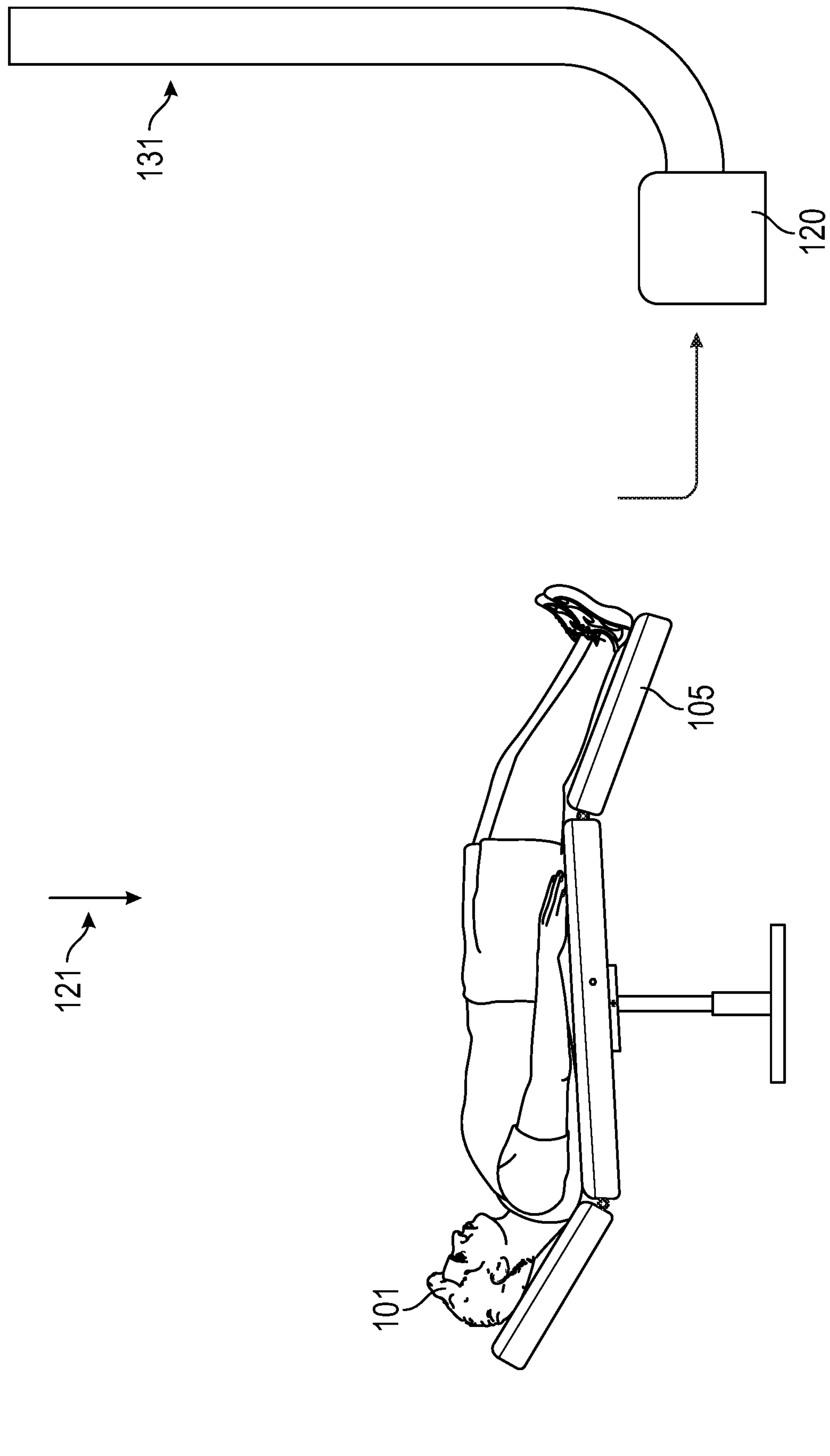
FIG. 1 is a schematic of a dental operatory, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Bioaerosols can be generated in any setting involving a human. For instance, the setting may be a seminar, a dinner, an emergency room setting, an interaction with a passerby, and the like.

Generation of bioaerosols in the dental setting, in particular, occur when high speed drills, ultrasonic devices, water/air sprays and high flow suctions are used in the performance of cutting procedures on the hard tissues and soft tissues of the oral cavity. These procedures require water and air irrigation to cool the surfaces of the instruments, with high-speed suction to evacuate the irrigation fluids. The irrigation fluids are mixed with saliva which can be tainted with bacterial and viral pathogens. The result is bioaerosols which leave the oral cavity at varying velocities and distances to contaminate the breathing zones of the nearby dental team and office environment.

The generation of bioaerosols in dentistry and the risk of transmission of contagious respiratory diseases has been a known risk for decades but mitigation has been focused on identifying those patients with disease and avoiding aerosolizing procedures on those patients. When dental aerosolizing procedures are required on a patient with a known respiratory disease (e.g., tuberculosis), the procedures are carried out in dedicated negative pressure rooms with dental team members fitted with at least N-95 masks and sealed eye protection.

Masks, in particular, are used in many clinical settings to avoid transmission of airborne particles between patient and clinician. However, masks restrict access to the patient during ear, nose, and throat (ENT) and dental procedures and may not be feasible in such scenarios. Further, dedicated negative pressure rooms, and other similarly equipped rooms for the performance of dentistry, are rarely available, even in tertiary medical care centers.

Moreover, as it particularly relates to novel coronavirus, even as the population of possibly contaminated people decreases, special facility designs, equipment, procedures and personal protective equipment continue to be required of dental operators in order to perform aerosolizing dental procedures.

Thus, until technology addresses the problem of bioaerosols as a risk to dental team members, patients, and the dental office environment at large, dentistry will remain a highest risk occupation.

Accordingly, the present disclosure describes a device for local control of an air volume for the prevention of disease transmission. The device, which may be referred to herein as an air control device, or ACD, may be configured to release a flow of air over a breathing zone of a dental patient in order to envelope and entrain bioaerosols generated by/via the dental patient during dental procedures, thereby protecting dental team members and the dental office environment. In an embodiment, such a fluidic shield of air flow may be supplemented by polymers configured to bind to pathogens that may be present in the air.

In an embodiment, the air control device would be placed between a clinician and a patient and would generate a high-velocity air flow to create a fluid barrier or shield between the subjects. The fluidic shield would primarily consist of filtered air but may also carry other sanitizing substances, such as triethylene glycol (TEG), to adsorb and entrain moisture particles in the air flow.

In an embodiment, the fluid of the fluidic barrier or the fluidic shield may be a gas or a liquid or other flowable material.

In an embodiment, the air control device may include a manifold set over the upper torso of a patient in a semi-reclined position on a dental chair, the manifold being configured to release a flow of air over a breathing zone of the patient. Further, the manifold may be configured to release harmless polymers within the air flow. In this way, contaminants in the breathing zone of the patient can be more readily entrained within the air flow and, subsequently, captured by a suction device positioned at a head of the patient.

In an embodiment, air, which may be filtered, can be delivered to the breathing zone of the patient via the manifold. The air may include a sanitizing substance, such as a polymer, and may be flowed in order to maintain a polymer envelope and prevent the polymer envelope from intruding into the breathing zone. By exploiting the Coanda effect, it can be appreciated that the introduction of hands and instruments into the mouth of the patient in the performance of dentistry will not interrupt the polymer flow.

In an embodiment, the polymers within the polymer envelope would include one or more of TEG, polyethylene glycol (PEG), and the like. TEG, in particular, is a compound used to disinfect and kill bacteria and viruses in hospitals and is generally recognized as safe by the EPA. Further, TEG is hygroscopic, allowing it to effectively bind airborne water droplets tainted with viral pathogens.

In an embodiment, the manifold can be shaped relative to a generalized contour of an upper torso of a patient.

According to an embodiment, a fluid shield (e.g. air shield, humidified air shield, liquid shield) generated by the air control device of the present disclosure has been shown to be capable of deflecting breath of a patient when the shield velocity exceeds the breath velocity at the point of impact, redirecting/deflecting moisture droplets carried in the breath from either side of the shield making it effective for patient and clinician, deflecting breath of a patient when a protruding object like a human hand or a clinical tool penetrates the air shield, and suspending and propelling TEG particles to intersect and interact with the breath of the users.

The air control device of the present disclosure will be critical equipment in the performance of dentistry and in any other professional setting requiring close face to face contact, especially those generating bioaerosols.

With reference now to the Figures, it can be appreciated that the air control device may be implemented within a dental operatory. A dental operatory may be evaluated using multivariate and configurable parameters of environmental parameters and engineering parameters as well as varying preparations of personal protective equipment and disinfectants.

In an embodiment, and as in FIG. 1, a dental operatory may include a patient 101 on a table 105, room-defined variables such as an air scrubber 120 in fluid communication with room air inflow 121 and room air outflow 131. Further to the above, it can be appreciated that a number of variables within the dental operatory may be modifiable in order to evaluate a number of working states of the dental operatory. For instance, the variables may include size, shape, and volume of the procedure room(s) and adjacent spaces, construction materials, ventilation, air flow, air change per hour, temperature, humidity, location of vents and diffusers, ceiling lights, ultraviolet (UV) lights, ionized air devices, professional equipment, water and air producing devices, drills (e.g., electric or pneumatic), high speed suction, low speed suction, open suction, closed suction, air source evacuators, negative pressure, positive pressure, mixed pressure, laminar pressure, wall textures, ceiling textures, flooring, window treatments, facility air curtains, PPE air curtains, door types, construction seams, and sources of penetrations, such as electrical outlets, vents, and projections, as well as disinfectant materials/application, among others. In an embodiment, the dental operatory may include, as variables, a number of dental professionals in the room, a type of dental procedure being performed and tools being used, patient health factors, as well as characteristics of potential types and load of pathogens that may be shed by one or more persons within the room. For instance, the types of pathogens may be airborne pathogens, such as novel coronaviruses, may be modeled using tagged particles such as fluorescein-tagged attenuated Influenza A virus. The tagged particles may be emitted as microdroplets of water from device(s) meant to simulate patients, doctors, and assistants, among others, breathing talking, coughing, and the like, with varying degrees of viral load, during the performance of common dental procedures.

In an embodiment, the dental operatory may be a simulated dental operatory, with standardized but configurable parameters, that can be used to evaluate, develop, and optimize environmental controls, equipment performance, and PPE which has been marketed, designed and/or considered to protect healthcare professionals.

Figure 2:
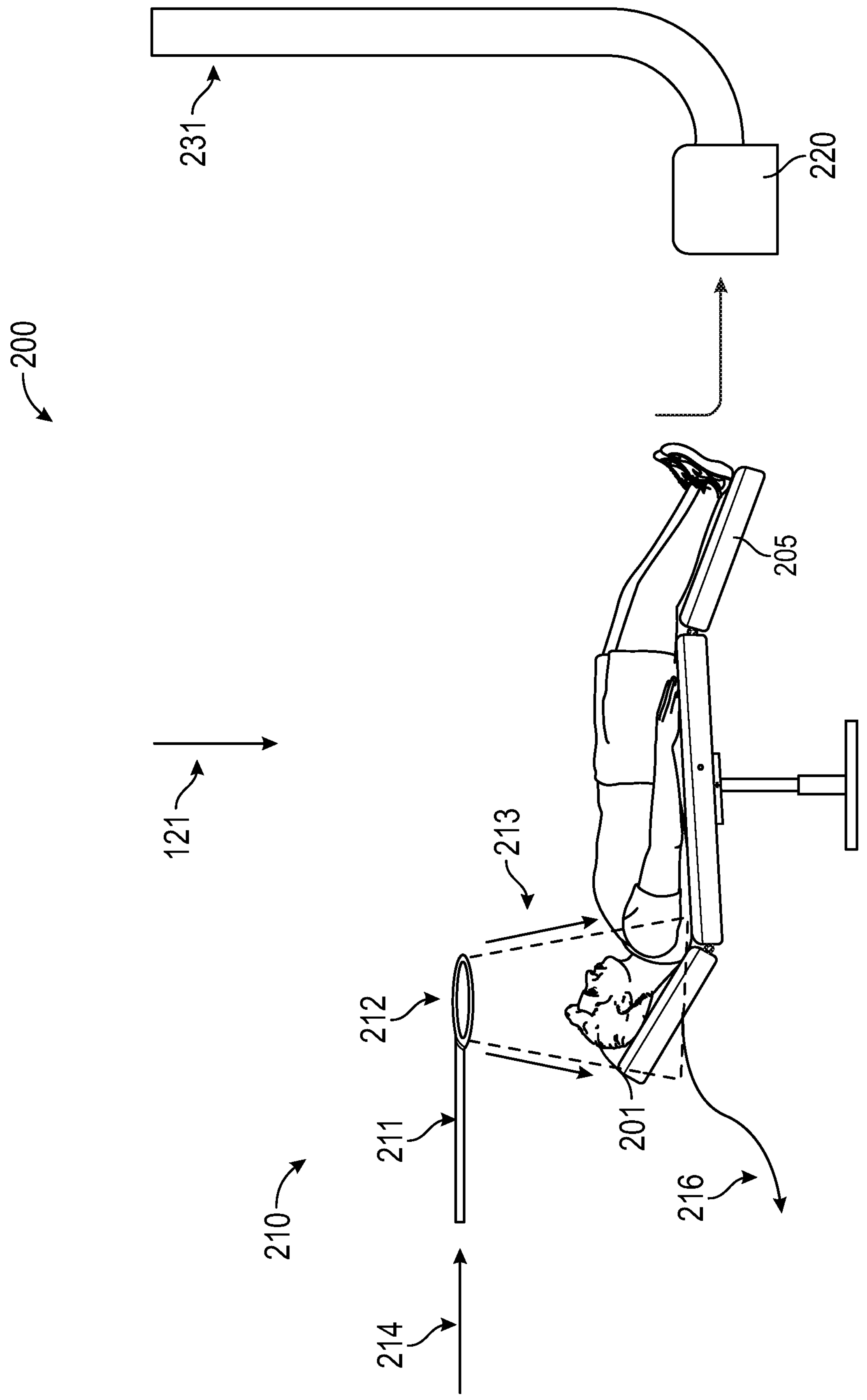
FIG. 2 is a schematic of an air control device implemented within a dental operatory, according to an exemplary embodiment of the present disclosure.
Figure 3A:
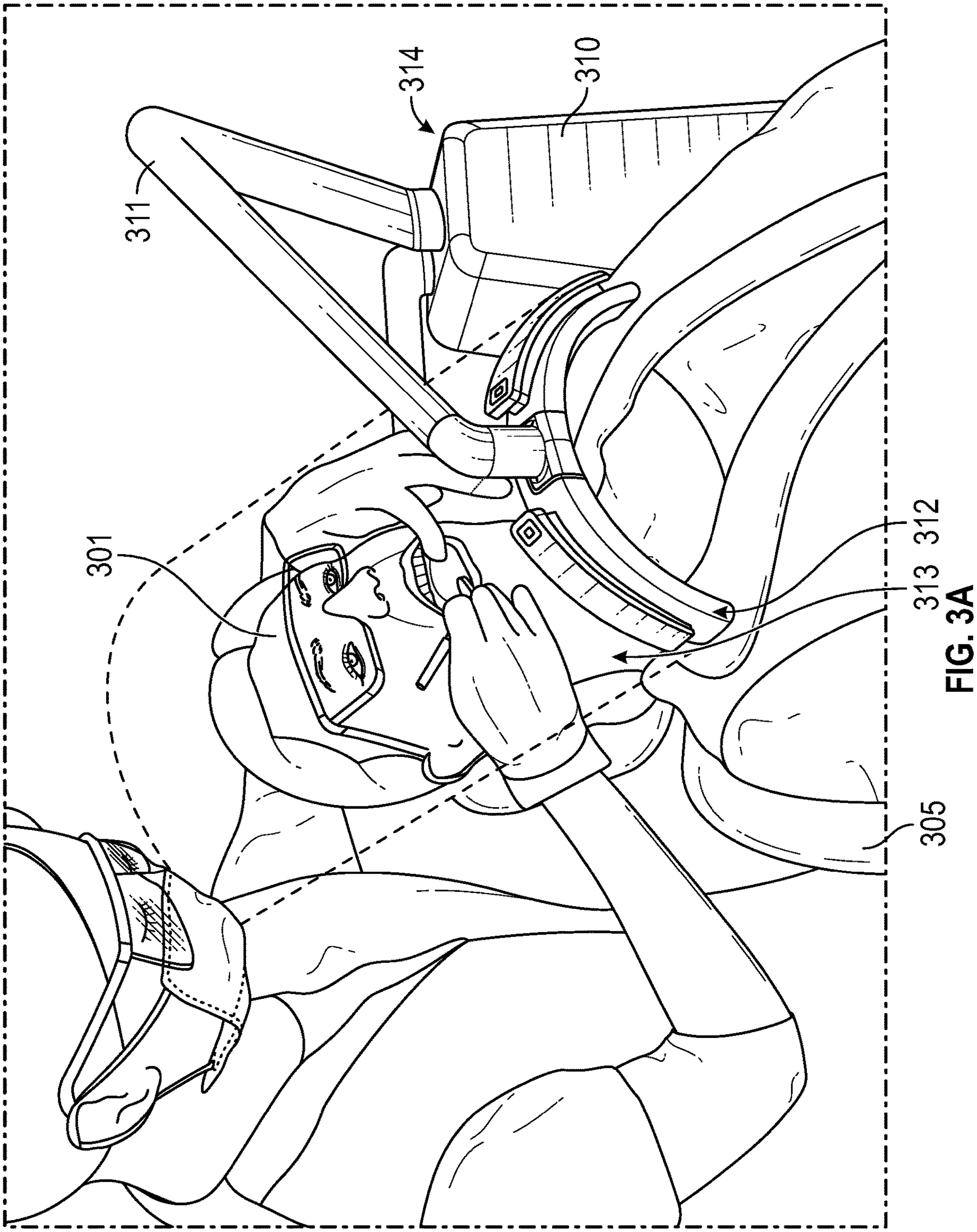
FIG. 3A is an illustration of an air control device implemented within a dental operatory, according to an exemplary embodiment of the present disclosure.
Figure 3B:
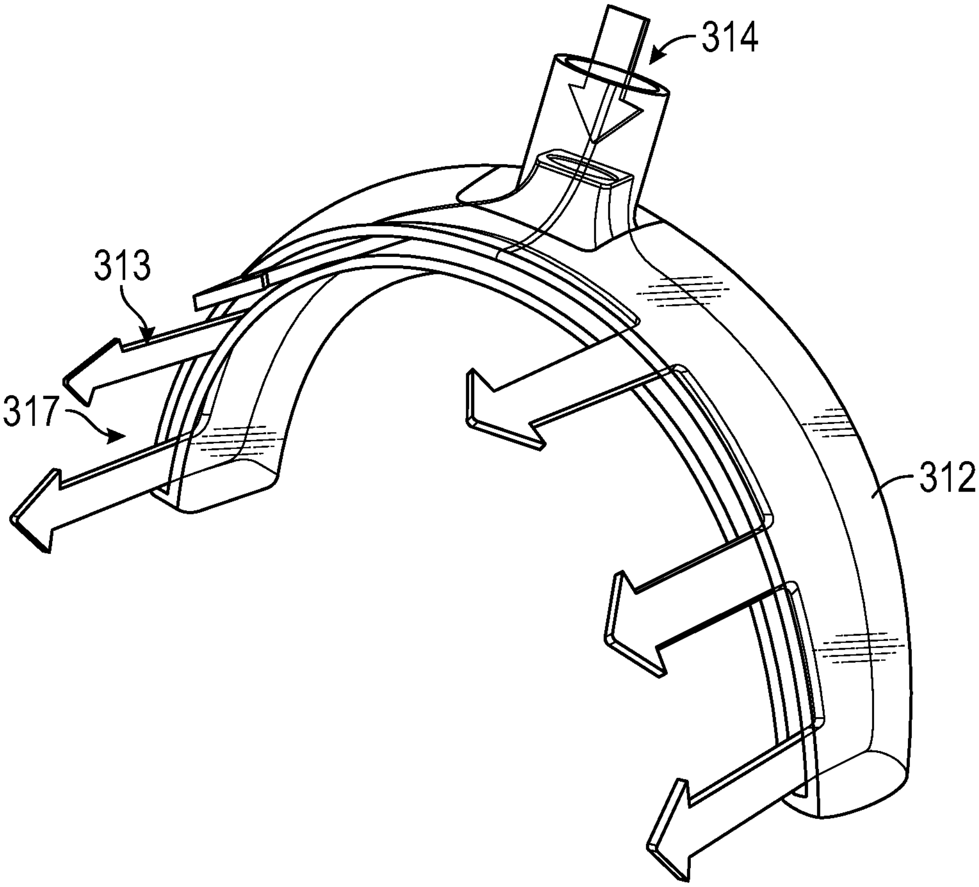
FIG. 3B is an illustration of an air control device implemented within a dental operatory, according to an exemplary embodiment of the present disclosure.

As in FIG. 2 through FIG. 3B, it can be appreciated that, accounting for the dental operatory factors and variables outlined above, the air control device of the present disclosure can deployed.

For instance, in an embodiment, the air control device can include a manifold that is manufactured in modules of a specified length (e.g., straight or curvilinear) with devices connected and sealed together. The ACD may include a console that may be a control device connected to a power supply mounted to a wall and/or a ceiling and connected to a fluid supply. In an embodiment, the console may be further interfaced and/or coordinated with the airflow dynamics, temperature, and humidity of the facility HVAC system. The system may include sensors configured to measure parameters of ambient air including airflow pressure, air humidity, air temperature, and air particulates.

The ACD may include networks of micro-tubing regulated by the manifold. The manifold may be arranged above the head of the patient, below the head of the patient, or around each side of the head of the patient, as is appropriate. The manifold may have a shape substantially that of a circle or some portion thereof, the circle or a portion of the circle (e.g. an arch) having a diameter or defining a diameter suitable to the head of the patient. In an example, the diameter may be approximately 20 cm. The manifold may be arranged based on a position of the head of the patient and the arrangement may be adjustable between different patients. In an example, the manifold may be arranged at 30 cm above the head of the patient or 30 cm below the head of the patient. In an embodiment, during use, a fluid stream of filtered air may be injected downward and outward to contain gaseous bioaerosols within a funnel-shaped air containment envelope around the head of the patient. The funnel-shaped air containment envelope may be defined by the downward and outward injection of fluid at an angle relative to an axis of the manifold, or at about 15 to 30 degrees relative thereto. Infrared light or other wavelength light projected from the ACD may image the water vapor or chemicals of envelope fluid for proper source positioning. In an embodiment, during use, a fluid stream of filtered air may be injected upward and outward to contain gaseous bioaerosols within a funnel-shaped air containment envelope around the head of the patient. The funnel-shaped air containment envelope may be defined by the upward and outward injection of fluid at an angle relative to an axis of the manifold, or at about 15 to 30 degrees relative thereto. Infrared light or other wavelength light projected from the ACD may image the water vapor or chemicals of envelope fluid for proper source positioning. Concurrently, the air containment envelope allows for the unimpeded insertion of dental workers arms, hands, and instruments in order to perform dental procedures. The Coanda effect maintains a seal around the penetration of the air containment envelope by arms and curvilinear objects.

In an embodiment, a suction device may be arranged opposite the manifold of the ACD in order to scavenge the bioaerosols safely from the field. In an example, through hydrogen bonds, pathogens may interact with dense air/fluid in the air containment envelope and be directed downward to lower pressure zones where a low speed suction device at the base of the funnel-shaped containment envelope will remove the bioaerosols safely from the field. Pathogens in the bioaerosols can be further degraded by aerosolized surfactants, chemicals, and electrically charged water vapor in a vacuum or collection chamber.

In an embodiment, a similar but more forceful ACD, with networks of micro-tubing regulated by computer-directed manifolds, may be implemented in order to frame laboratory work spaces and contain fumes, debris, and bioaerosols generated when patient dental devices are modified or cleaned with rotary devices.

In an embodiment, the ACD may include visual alarms and audible alarms with central controls to detect failures within a network of air containment envelopes.

In particular, and with reference now to FIG. 2, an ACD may be deployed in a dental operatory to isolate a patient's head from the medical staff, according to an exemplary embodiment of the present disclosure. For instance, a patient 201 may be on a table 205 within a dental operatory 200. The dental operatory 200 may include, among other items, a room air inflow 221, an air scrubber 220, and a room air outflow 231. An air control device 210 (ACD) may be arranged above a region of interest of the patient 201 or, in particular, a head of the patient 201. The ACD 210 may include a power supply and a lumen 211 connected to a fluid supply 214 and configured in fluid communication with a manifold 212, the manifold 212 having a plurality of apertures for distributing a fluid from the fluid supply 214 to the patient. The ACD 210 may further include one or more patient sensors, in certain implementations. The plurality of apertures may be distributed at equal distances around a diameter of the manifold 212. The distributed fluid may form a fluid envelope 213 around the head of the patient 201. Air contained within the fluid envelope 213 may be evacuated from the dental operatory via vacuum 216. In an embodiment, the fluid supply 214 may be an air supply supplied at a predefined pressure and/or a predefined humidity. The predefined pressure may be 250 mBar, in an example, in order to generate a high pressure area within the air containment envelope. Further, a filter may be supplied within the ACD 210 on one side of the head of the patient 201 or may be supplied within the vacuum 216. In an example, the filter is a HEPA filter and is installed within the ACD 210 device to provide filtered fluid to the fluid envelope 213.

In an embodiment, the plurality of apertures of the manifold 212 may be individually maneuverable according to a position of the head of the patient 201 and a desired volume of the fluid envelope 213. Each of the plurality of apertures may be configured to adapt to a position of the head of the patient. In this way, the plurality of apertures may generate the fluid envelope 213 in a number of volumes relative to the manifold 212. Moreover, as in the example of FIG. 2, the plurality of apertures may be configured to generate the fluid envelope 213 such that the fluid envelope 213 has an outer angle relative to a normal axis passing through the manifold 212. This can be accomplished by arranging the plurality of apertures at an angle relative to the normal axis of the manifold 212. The outer angle may be 15°, in an example, or any angle appropriate for enveloping a region of interest of the patient 201 and providing air containment therein, such as 30°.

In an embodiment, the manifold 212 may have a geometric form according to a demand of the implementation. For instance, as in the dental operatory 200 of FIG. 2, it is important to generate the air/fluid envelope 213 around the head of the patient 201 such that a circular curtain is formed. In this way, the manifold 212 may have a circular shape. However, it can be appreciated that any shape or combination of shapes may be implemented within the manifold 212, including linear structures, curvilinear structures, and a variety of closed structures such as a square, rectangle, and triangle.

In an embodiment, the fluid supply 214 includes air, water, and surfactant, combinations of which can be controlled and provided in order to generate a specific air containment envelope about a region of interest of the patient 201.

In an embodiment, the one or more position sensors of the ACD 210 may be a proximity sensor able to detect a region of interest of the patient 201. For instance, the proximity sensor may be a Bluetooth sensor or may emit an electromagnetic signal, such as an infrared signal, in order to determine a heat level of a target and to, accordingly, identify the region of interest of the patient 201.

Figure 7:
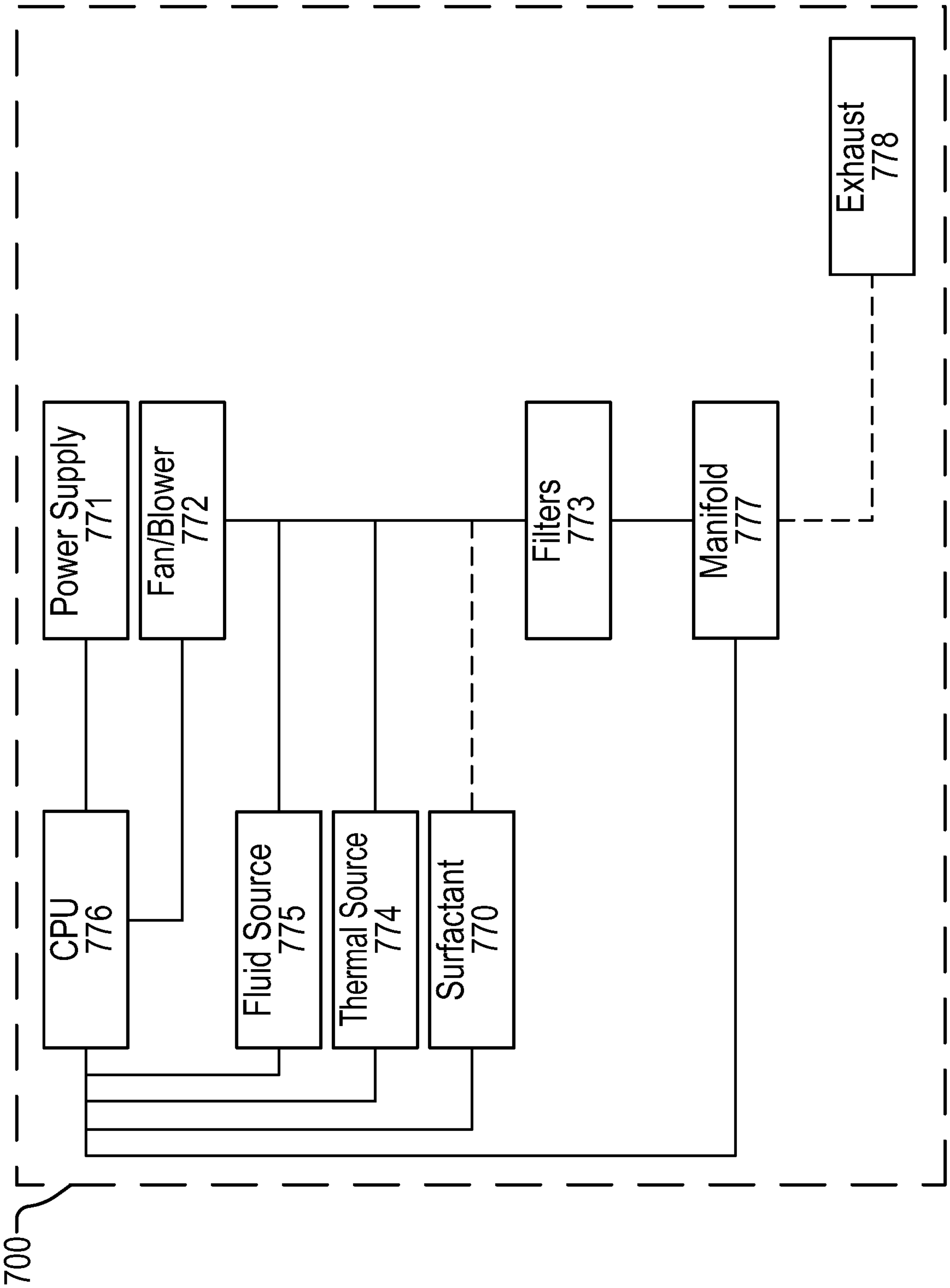
FIG. 7 is a hardware schematic of an air control device, according to an exemplary embodiment of the present disclosure.

In an embodiment, upon identification of a position of a target via the one or more position sensors, the plurality of apertures of the manifold 212 may be rearranged to focus on the target relative to the normal axis of the manifold 212 using electric motors or the like A schematic of the ACD, including processing circuitry configured to control the ACD and components thereof, is provided with reference to FIG. 7.

As a variation of FIG. 2, FIG. 3A and FIG. 3B provide illustrations of an ACD deployed in a dental operatory to isolate a patient's head from the medical staff, according to an exemplary embodiment of the present disclosure.

In an embodiment, the present disclosure describes a device that may be worn by the user or suspended in proximity of the head. Generally, the device consists of a nozzle directing fluid flow in front of the face of a user. The fluid creates a barrier ("fluidic shield") between the user and their surroundings and is intended to direct the breath and any respiratory droplets away from others. The fluid is primarily filtered air supplied by a stationary pressure source. Other fluids with hygroscopic or disinfecting properties may be injected into the air stream to capture or neutralize droplets or particles entrained by the fluidic shield.

More specifically, and as it relates to FIG. 3A and FIG. 3B, a patient 301 may be on a table 305 within a dental operatory. The dental operatory may include, among other items, a room air inflow, an air scrubber, and a room air outflow. An air control device 310 (ACD) may be arranged relative to a region of interest of the patient 301 or, in particular, a head of the patient 301. The ACD 310 may include a power supply and a lumen 311 connected to a fluid supply 314 and configured in fluid communication with a manifold 312, the manifold 312 having a plurality of apertures 317 for distributing a fluid from the fluid supply 314 to the patient, as shown in FIG. 3B. The ACD 310 may further include one or more patient sensors, in certain implementations. The plurality of apertures 317 may be distributed at equal distances around a diameter of the manifold 312. The distributed fluid may form a fluid envelope 313 around the head of the patient 301. Air contained within the fluid envelope 313 may be evacuated from the dental operatory via vacuum or may dissipate and be diluted into ambient air. In an embodiment, the fluid supply 314 may be an air supply supplied at a predefined pressure and/or a predefined humidity. The predefined pressure may be 250 mBar, in an example, in order to generate a high pressure area within the air containment envelope. Further, a filter may be supplied within the ACD 310 on one side of the head of the patient 301 or may be supplied within the vacuum. In an example, the filter is a HEPA filter and is installed within the ACD 310 device to provide filtered fluid to the fluid envelope 313.

In an embodiment, the plurality of apertures 317 of the manifold 312 may be individually maneuverable according to a position of the head of the patient 301 and a desired volume of the fluid envelope 313. Each of the plurality of apertures may be configured to adapt to a position of the head of the patient. In this way, the plurality of apertures 317 may generate the fluid envelope 313 in a number of volumes relative to the manifold 312. Moreover, the plurality of apertures 317 may be configured to generate the fluid envelope 313 such that the fluid envelope 313 has an outer angle relative to a normal axis passing through the manifold 312. This can be accomplished by arranging the plurality of apertures 317 at an angle relative to the normal axis of the manifold 312. The outer angle may be 15°, in an example, or any angle appropriate for enveloping a region of interest of the patient 301 and providing air containment therein, such as 30°.

In an embodiment, the manifold 312 may have a geometric form according to a demand of the implementation. For instance, as in the dental operatory of FIG. 3A, it is important to generate the air/fluid envelope 313 around the head of the patient 301 such that a circular curtain is formed. In this way, the manifold 312 may have a circular shape. However, it can be appreciated that any shape or combination of shapes may be implemented within the manifold 312, including linear structures, curvilinear structures, and a variety of closed structures such as a square, rectangle, and triangle.

In an embodiment, the fluid supply 314 includes air, water, and surfactant, combinations of which can be controlled and provided in order to generate a specific air containment envelope about a region of interest of the patient 301.

In an embodiment, the one or more position sensors of the ACD 310 may be a proximity sensor able to detect a region of interest of the patient 301. For instance, the proximity sensor may be a Bluetooth sensor or may emit an electromagnetic signal, such as an infrared signal, in order to determine a heat level of a target and to, accordingly, identify the region of interest of the patient 301.

In an embodiment, upon identification of a position of a target via the one or more position sensors, the plurality of apertures 317 of the manifold 312 may be rearranged to focus on the target relative to the normal axis of the manifold 312 using electric motors or the like A schematic of the ACD, including processing circuitry configured to control the ACD and components thereof, is provided with reference to FIG. 7.

Figure 3C:
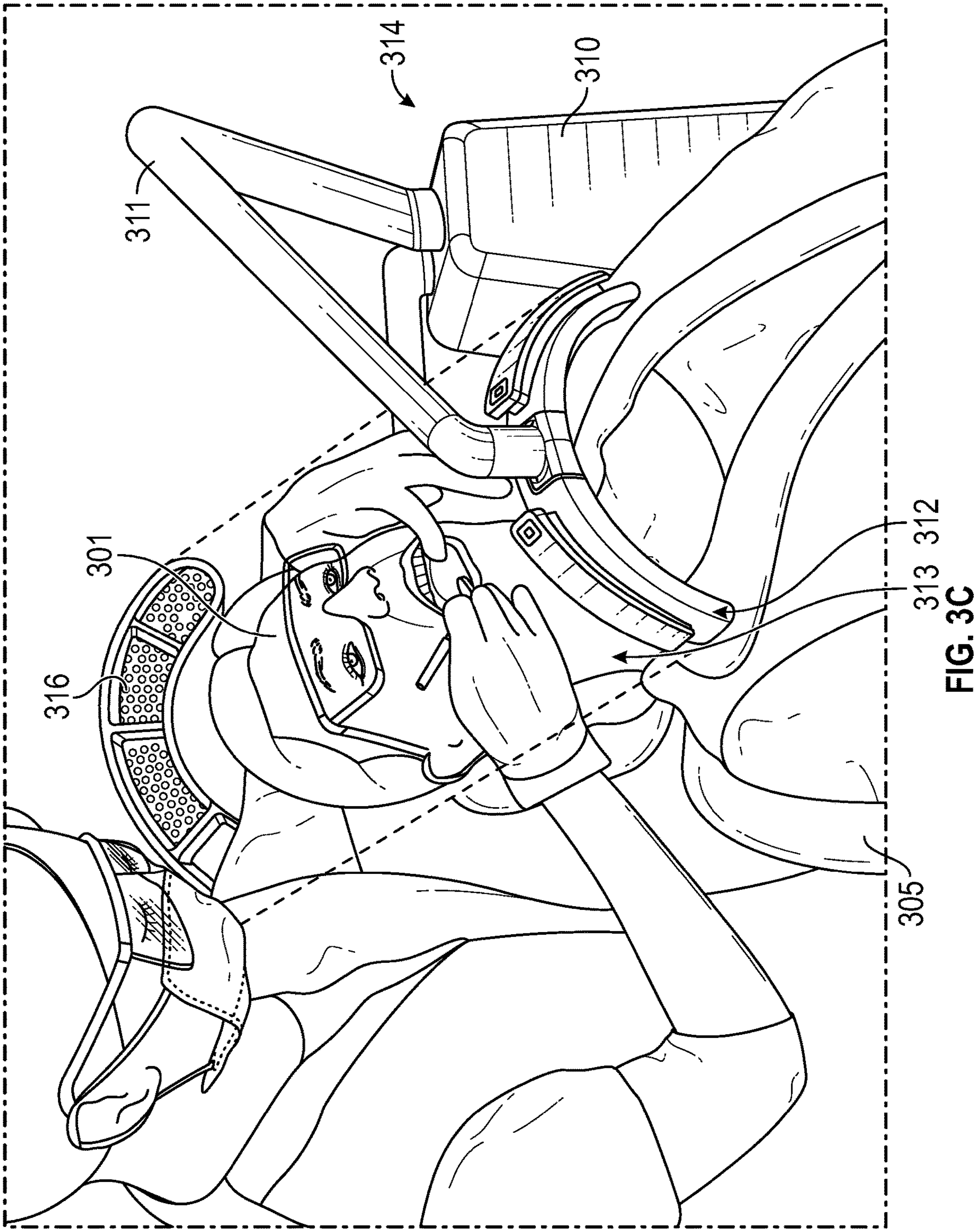
FIG. 3C is an illustration of an air control device implemented within a dental operatory, according to an exemplary embodiment of the present disclosure.

FIG. 3C provides an additional description of the present disclosure, wherein an ACD may be deployed in a dental operatory to isolate a patient's head from the medical staff, according to an exemplary embodiment. For instance, a patient 301 may be on a table 305 within a dental operatory. The dental operatory may include, among other items, a room air inflow, an air scrubber, and a room air outflow. An air control device 310 (ACD) may be arranged relative to a region of interest of the patient 301 or, in particular, a head of the patient 301. The ACD 310 may include a power supply and a lumen 311 connected to a fluid supply 314 and configured in fluid communication with a manifold 312, the manifold 312 having a plurality of apertures for distributing a fluid from the fluid supply 314 to the patient. The ACD 310 may further include one or more patient sensors, in certain implementations. The plurality of apertures may be distributed at equal distances around a diameter of the manifold 312. The distributed fluid may form a fluid envelope 313 around the head of the patient 301. Air contained within the fluid envelope 313 may be evacuated from the dental operatory via vacuum 316. In an embodiment, the fluid supply 314 may be an air supply supplied at a predefined pressure and/or a predefined humidity. The predefined pressure may be 250 mBar, in an example, in order to generate a high pressure area within the air containment envelope. Further, a filter may be supplied within the ACD 310 on one side of the head of the patient 301 or may be supplied within the vacuum 316. In an example, the filter is a HEPA filter and is installed within the ACD 310 device to provide filtered fluid to the fluid envelope 313.

ACDs, such as that described above, include networks of pressurized fluid within micro-tubes enclosed in channels with computer-controlled manifold systems for generation of air containment envelopes within in a room. The fluid may be air, liquid, or other flowable material. The air containment envelope may be generated by pressurized air, water vapor, and aerosolized surfactant. To direct airflow to form the air containment envelope, airflow is projected in a continuous slit stream of fluid, which flows more like a "wave" of cohesive low density liquid, within a media of lower density liquid. To further enhance the "wave" projection, successive loads of fluid can be air "pistoned" forward in a manner similar to decorative water fountains. Noise generated by jet streams of fluid can be canceled by a manner similar to noise canceling headphones (e.g., equal but opposite sound waves).

In this way, and in view of the above, ACDs provide an invisible barrier ideal for the containment of bioaerosols.

It can be appreciated that any technology developed to mitigate viral airborne threats in dentistry will be embraced by dental professionals, mandated by regulators, and may incubate an entirely new industry which can expand to mitigate viral airborne threats in fields other than dentistry such as medicine, meat processing plants, office spaces, sport arena seating, movie theaters, restaurants, public transportation, airlines, cruise ships and many other venues. Such venues include military government educational institutions, essential businesses, hotels, retail stores, theme parks, casinos, manufacturing centers, apartment condominium common areas, churches, theaters, food outlets, and the like.

To this end, ACDs may be deployed in a variety of settings. For instance, in a nursing home, an ACD may be mounted on the ceiling over the resident in bed and/or over the resident while sitting or in the dining room, and may provide an invisible protective envelope from bioaerosol transmission for the resident, staff, and visitors.

To make this possible, the ACD can be spatially arranged around room occupant(s) in a specific manner based on a particular venue and may deploy corrective measures to create a protective microclimate around room occupant(s), accordingly. By optimizing features of controlling airflow, water vapor, and surfactant, ACDs are scalable to any size and venue, as will be exemplified with reference to FIG. 4 through FIG. 6.

Figure 4:
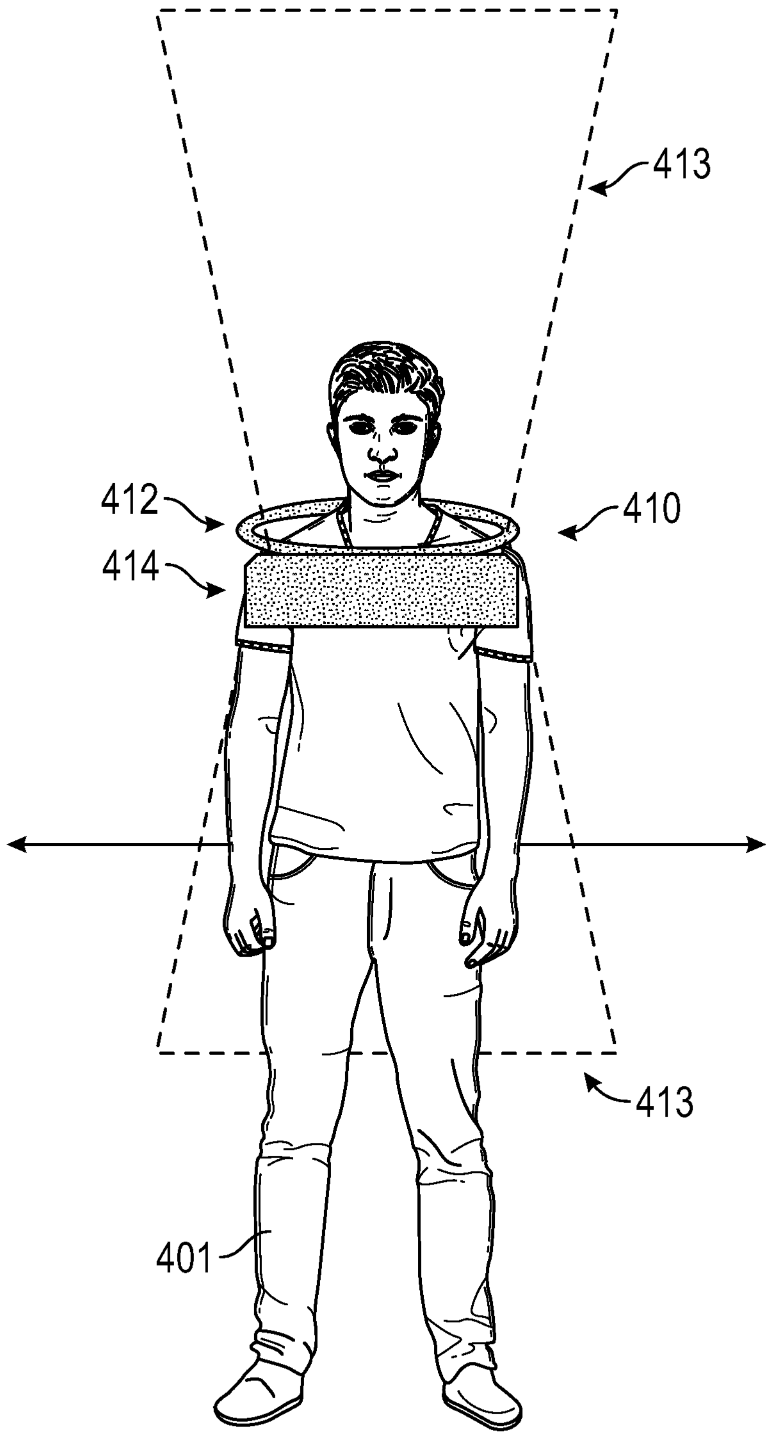
FIG. 4 is a schematic of an air control device implemented within personal space of a standing person, according to an exemplary embodiment of the present disclosure.

With reference to FIG. 4, an ACD 410 may be a wearable device appropriate for daily wear and may include a manifold 412, a fluid supply 414, and mobile power supply connected to processing circuitry configured to control the ACD 410. The ACD 410 may be arranged around a neck of a subject 401 in order to generate a fluid envelope 413 that encompasses a microclimate of the subject 401. In an embodiment, the ACD 410 may further include a low pressure exhaust system configured to expel disinfected exhaust from the microclimate of the subject 401. It can be appreciated that the ACD 410 may include other features described with reference to FIG. 2 through FIG. 3B.

Figure 5:
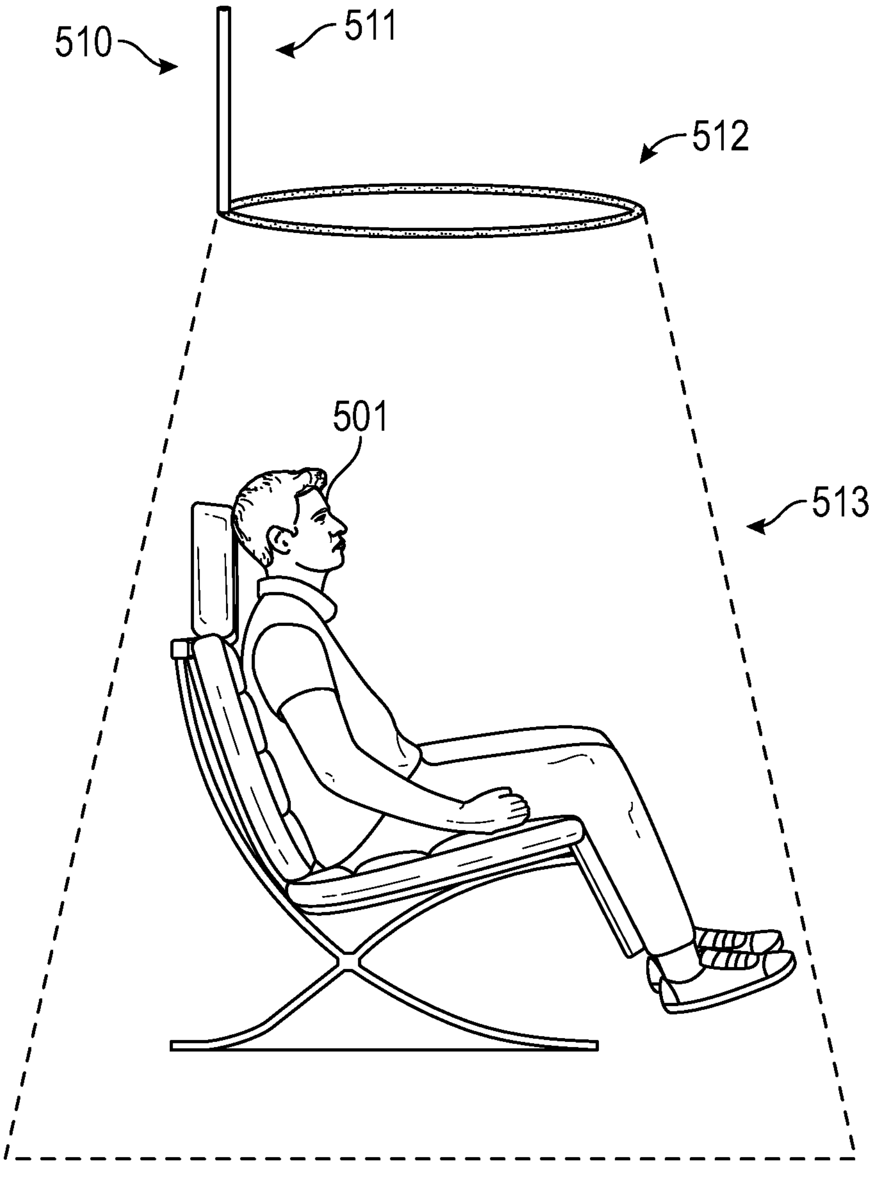
FIG. 5 is a schematic of an air control device implemented within personal space of a seated person, according to an exemplary embodiment of the present disclosure.

With reference to FIG. 5, an ACD 510 may be configured to generate an air containment envelope from above a subject 501 and may be appropriate for an airplane seat, a theater seat, and/or concert or sports stadium seating. The ACD 510 may include a manifold 512, a lumen 511 connected to a fluid supply, and power supply connected to processing circuitry configured to control the ACD 510. The ACD 510 may be arranged above a subject 501 in order to generate a fluid envelope 513 that encompasses a microclimate of the subject 501. In an embodiment, the ACD 510 may further include a low pressure exhaust system configured to expel disinfected exhaust from the microclimate of the subject 501. It can be appreciated that the ACD 510 may include other features described with reference to FIG. 2 through FIG. 3B.

Figure 6:
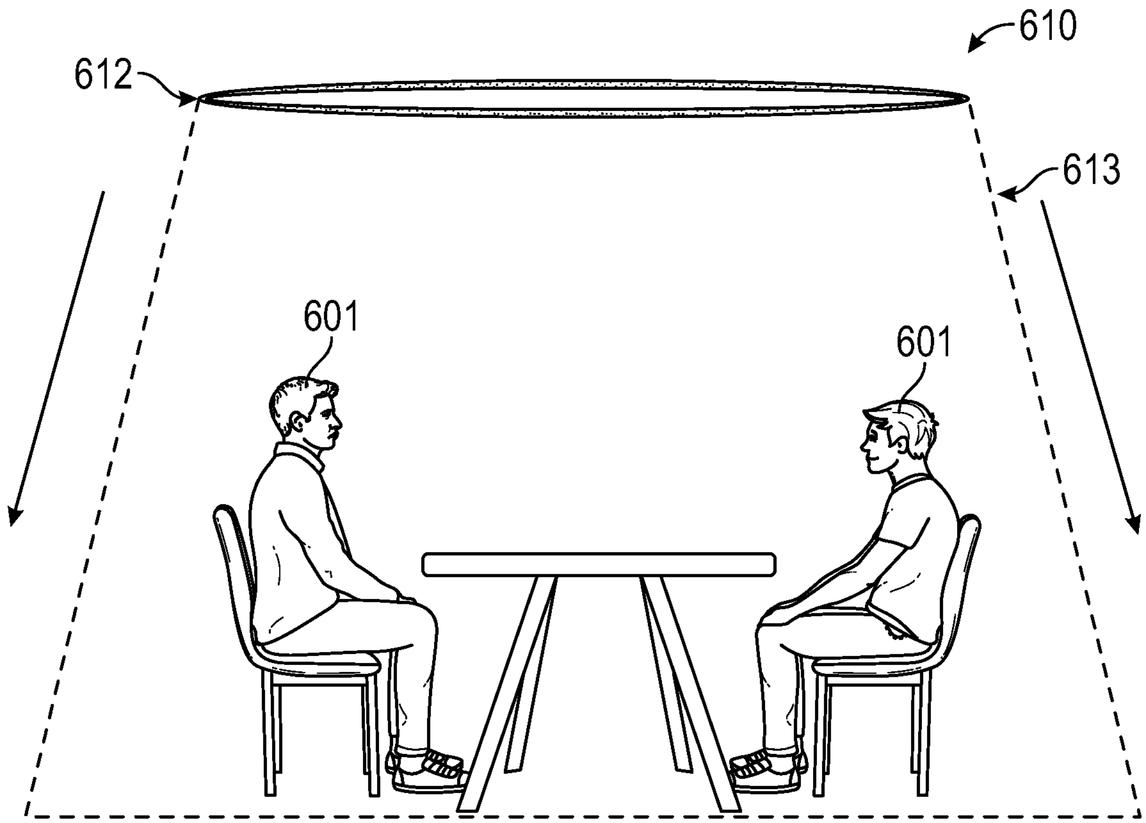
FIG. 6 is a schematic of an air control device implemented within a space of one or more persons, according to an exemplary embodiment of the present disclosure.

With reference to FIG. 6, an ACD 610 may be configured to generate an air containment envelope from above one or more subjects 601 and may be appropriate for a restaurant, office, and/or cruise ship setting. The ACD 610 may include a manifold 612, a fluid supply, and power supply connected to processing circuitry configured to control the ACD 610. The ACD 610 may be arranged above the one or more subjects 601 in order to generate a fluid envelope 613 that encompasses a microclimate of the one or more subjects 601. In an embodiment, the ACD 610 may further include a low pressure exhaust system configured to expel disinfected exhaust from the microclimate of the one or more subjects 601. It can be appreciated that the ACD 610 may include other features described with reference to FIG. 2 through FIG. 3B.

According to an embodiment, an ACED may continuously monitor and display all components of device performance through cell phone technology. Wireless communication technology, such as Bluetooth® k), may alert individuals of air containment envelope protection either as an individual or when entering a venue offering broader air containment envelope protection, such as retail stores, schools, banks, theaters, healthcare facilities, and the like. Depending on community viral threat level (e.g., mild or high), venue viral threat level (e.g., A, B, C or rating) and an individual's tolerance to the viral threat, layers of air containment envelopes can be added or subtracted.

In an embodiment, parameters of ambient air can be evaluated through sensors. For instance, air pressure, air direction, humidity, temperature, and air particulates can be measured.

In an embodiment, an ACD can be configured to deploy corrective measures to create a protective microclimate around room occupant(s).

In view of the above, it can be appreciated that air, for instance, is a low density fluid. An ACD directs airflow, enriched into a higher density fluid with moisture and disinfectant, to generate an air containment envelope and to protect an occupant(s). ACDs exploit the knowledge that higher air pressure directs airflow, higher humidity scavenges microdroplets by hydrogen bond affinity and directs particles below breathing zone by gravity, and detergents in enhanced airflow kill airborne pathogens.

With reference now to FIG. 7, a non-limiting example of a control device for an ACD will now be described. An ACD 700 may include a power supply 771 coupled to a central processing unit (CPU) 776 and a fan/blower 772. The CPU 776 may be configured to control a fluid source 775, a thermal source 774, and a disinfectant source 770. The fluid source 775 may be a gas or a liquid and may be pressurized. The fluid source 775 may also be an existing laminar air flow system already built into a room structure, or a source of compressed or pressurized air. In one embodiment, there is a pre-filter that excludes particles of 5 microns or more, for example. The filtered air may optionally be passed through another filter that excludes bacteria and other microbes such as fungi and viruses. A filter with a porosity of 0.22-0.30 μm or less would be suitable for the second stage filter. Alternatively, one or more filters with 0.22-0.30 μm can be used. The thermal source 774 may be a heat generator for warming a fluid of the fluid source 775. The fluid of the fluid source 775 can be heated by any means known to those skilled in the art of heating air, such as a resistive element or heater near the air. The disinfectant source 770 may include surfactants and sterile solutions of antimicrobial or antibiotic agents that can be mixed with the air before or after filtration so that a germicidal effect is afforded to the fluid envelope. Suitable anti-microbial agents include antibiotics, triclosan, ethanol, or chlorhexidene gluconate in concentrations of 0.1-1.0 percent in a sterile saline or suitable physiological buffer such as phosphate buffered saline. In addition, nebulized mists of anti-microbial solutions to further retard bacterial survival can also be utilized. Fluid passed through filters 773 can be delivered to a manifold 777 having a plurality of apertures and which is controlled by the CPU 776 to generate an air containment envelope. The manifold 777 may include one or more position sensors, in an example, to detect a target and in order to adjust an orientation of the plurality of apertures of the manifold 777. Pathogenic material entrapped within the generated air containment envelope may be collected via exhaust 778. The air containment envelope may be provided at any appropriate speed. For instance, the air containment envelope can be provided at a speed as described with reference to the below Non-Limiting Experimental Results.

Figure 8:
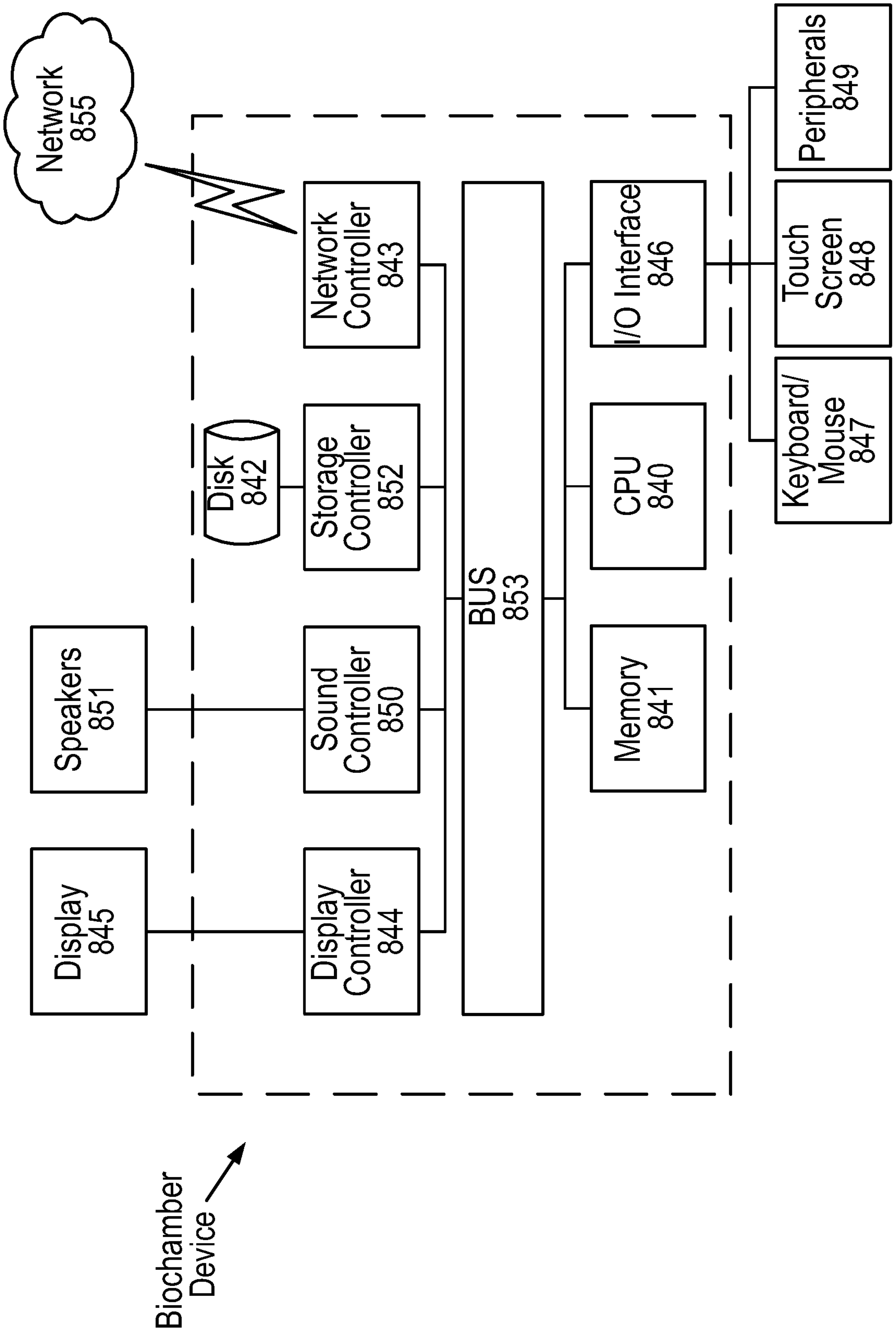
FIG. 8 is a hardware schematic of processing circuitry of a biochamber device, according to an exemplary embodiment of the present disclosure.

Next, a hardware description of the biochamber device of FIG. 1, according to exemplary embodiments, is described with reference to FIG. 8. In FIG. 8, the biochamber device includes a CPU 840 which performs the processes described above/below. The process data and instructions may be stored in memory 841. These processes and instructions may also be stored on a storage medium disk 842 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory. RAM, ROM, PROM, EPROM, EEPROM, hard disk or any other information processing device with which the biochamber device communicates, such as a server or computer.

Further, the claimed advancements may be provided as a utility application, background daemon, or component of an operating system, or combination thereof, executing in conjunction with CPU 840 and an operating system such as Microsoft Windows, UNIX, Solaris, LINUX, Apple MAC-OS and other systems known to those skilled in the art.

The hardware elements in order to achieve the biochamber device may be realized by various circuitry elements, known to those skilled in the art. For example, CPU 840 may be a Xenon or Core processor from Intel of America or an Opteron processor from AMD of America, or may be other processor types that would be recognized by one of ordinary skill in the art. Alternatively, the CPU 840 may be implemented on an FPGA, ASIC. PLD or using discrete logic circuits, as one of ordinary skill in the art would recognize. Further, CPU 840 may be implemented as multiple processors cooperatively working in parallel to perform the instructions of the inventive processes described above.

The biochamber device in FIG. 8 also includes a network controller 843, such as an Intel Ethernet PRO network interface card from Intel Corporation of America, for interfacing with network 855. As can be appreciated, the network 855 can be a public network, such as the Internet, or a private network such as an LAN or WAN network, or any combination thereof and can also include PSTN or ISDN sub-networks. The network 855 can also be wired, such as an Ethernet network, or can be wireless such as a cellular network including EDGE, 3G and 4G wireless cellular systems. The wireless network can also be WiFi, Bluetooth. or any other wireless form of communication that is known.

The biochamber device further includes a display controller 844, such as a NVIDIA GeForce GTX or Quadro graphics adaptor from NVIDIA Corporation of America for interfacing with display 845, such as a Hewlett Packard HPL2445w LCD monitor. A general purpose I/O interface 846 interfaces with a keyboard and/or mouse 847 as well as a touch screen panel 848 on or separate from display 845. General purpose I/O interface also connects to a variety of peripherals 849 including printers and scanners, such as an OfficeJet or DeskJet from Hewlett Packard.

A sound controller 850 is also provided in the biochamber device, such as Sound Blaster X-Fi Titanium from Creative, to interface with speakers/microphone 851 thereby providing sounds and/or music.

The general purpose storage controller 852 connects the storage medium disk 842 with communication bus 853, which may be an ISA, EISA, VESA, PCI, or similar, for interconnecting all of the components of the biochamber device. A description of the general features and functionality of the display 845, keyboard and/or mouse 847, as well as the display controller 844, storage controller 852, network controller 843, sound controller 850, and general purpose I/O interface 846 is omitted herein for brevity as these features are known.

Non-Limiting Experimental Results

To demonstrate feasibility of the above-described ACD, a series of theoretical evaluations were performed based on a developed model of the ACD.

In order to create a model of the fluidic shield, it was assumed that the air flow is oriented upward from the chest of the user. An upward flow also allows for sufficient space to add a suction device to collect the users' breath for filtering, if desired. The flow which forms the shield external to the collar is modeled.

As will be realized below, the person on the concave side of ACD is sometimes called the patient and the person on the convex side of the ACD is called the clinician. The choice of terminology is arbitrary and the conclusions are equally valid with the reverse assumptions.

Figure 9:
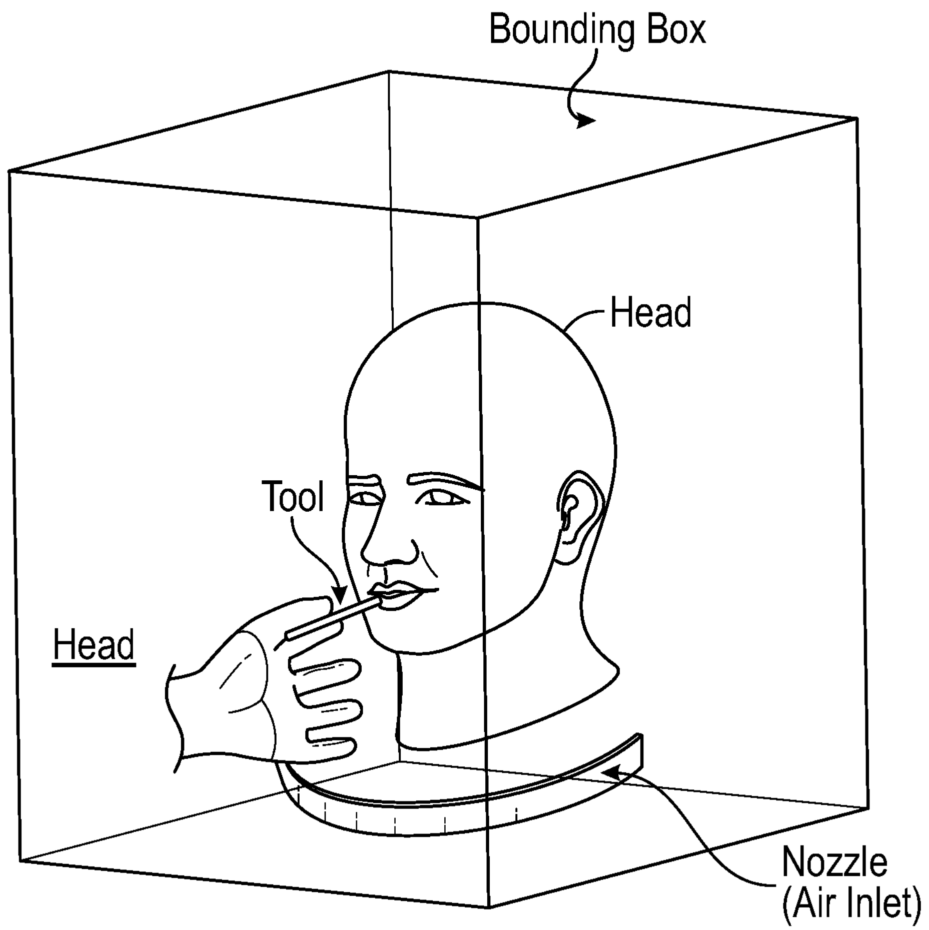
FIG. 9 is an illustration of a simulation model for evaluating an air control device implemented within a dental operatory, according to an exemplary embodiment of the present disclosure.
Figure 10:
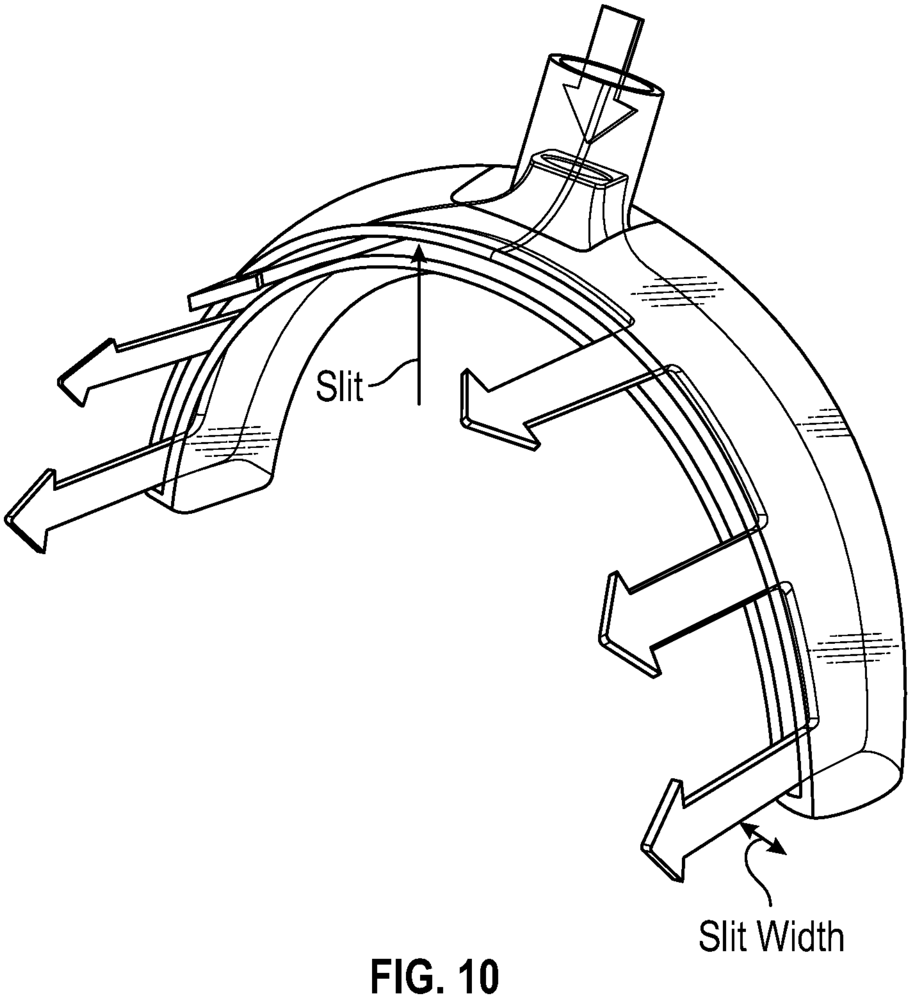
FIG. 10 is an illustration of an air control device implemented within a dental operatory, according to an exemplary embodiment of the present disclosure.

The model used in computational fluid dynamics simulations consists of a human head and of a hand holding a tool and reaching toward the face originating from the convex side of the shield, as shown in FIG. 9. It also includes a curved nozzle, as in FIG. 10 and similarly presented in FIG. 3B, that provides the air flow to develop the shield. The model was chosen to mimic typical patient-clinician interaction in a dentistry setting. The model is bounded by a rectangular box.

The efficacy of the fluidic shield is dependent on a number of design and operating parameters. Such design and operating parameters can be selected in order to satisfy certain objectives. For instance, such parameters may include slit exit air speed, slit width, size of chemical aerosol, droplets in breath, and whether the patient is coughing. The slit exit air speed relates to a relationship defining the ability of the fluidic shield to divert breath streams, wherein the ability of the fluidic shield to divert breath streams is proportional to the slit exit air speed. The slit width relates to a relationship defining a robustness of the fluidic shield, wherein the robustness of the fluidic shield is dependent on the shield mass flow, which is proportional to the slit width (i.e., thickness). The size of chemical aerosol may be based on a specific hygroscopic or disinfectant fluid injected into the shield air stream to serve as a secondary barrier against transmission between patient and clinician. The hygroscopic or disinfectant fluid may be, for instance TEG (0.5% to 20%). The droplets in breath relate to water droplets contained within either of the patient's or the clinician's breath. To investigate how droplets are transported by each breath, two sizes of respiratory droplets are simulated for the patient's breath and one droplet size is simulated for the clinician's breath. As it relates to a coughing patient, a cough ejects air at higher velocity than normal breathing and is likely to challenge the integrity of the fluidic shield.

The considerations above are investigated within the limits shown in Table 1. The relevant parameters are combined into eight simulation cases as follows (letter labels refer to the rows in Table 1 while the numeric labels designate the corresponding column): (1) A1B1—Slow air speed and narrow slit; (2) A2B1—High air speed and narrow slit; (3) A2B2—High air speed and wide slit2; (4) A2B1C2D1—High air speed, narrow slit, large TEG particles injected from device, and small moisture droplets contained in the patient's breath; (5) A2B1C2D2—High air speed, narrow slit, large TEG particles injected from device, and large moisture droplets contained in the patient's breath; (6) A2B1C2D1E—High air speed, narrow slit, large TEG particles injected from device, small moisture droplets contained in the patient's breath, and medium moisture droplets contained in the clinician's breath; (7) A2B1D1F1—High air speed, narrow slit, weak cough by the patient transporting small moisture droplets; and (8) A2B1D1F2—High air speed, narrow slit, strong cough by the patient transporting small moisture droplets.

TABLE 1

| Case | Description | Parameter Range<br>1<br>Minimum Value | <br>2<br>Maximum Value |
|---|---|---|---|
| A | Slit Air Speed at Collar | 3 m/s (6.7 mph) | 15 m/s (33.6 mph) |
| B | Slit Width | 3 mm (0.12 in) | 6 mm (0.24 in) |
| C | Injection of TEG Particles from Device Slit | 1.26 μm ($5 \times 10^{-5}$ in) | 3.72 μm ($1.5 \times 10^{-4}$ in) |
| D | Injection of Water Droplets from Patient's Mouth | 0.3 μm ($1.2 \times 10^{-5}$ in) | 10 μm ($3.9 \times 10^{-4}$ in) |
| E | Injection of Water Droplets from Clinician's Side | 1.0 μm ($3.9 \times 10^{-5}$ in) | |
| F | Coughing Patient (Includes Small Water Droplets) | 2.2 m/s (4.9 mph) | 10 m/s (22.4 mph) |

In view of the above, computational fluid dynamic studies were performed under the following assumptions: (1) That the air flows vertically upward from the nozzle from a semi-circular slit on a curved collar. This upward flow modeling avoids impingement of the flow on the patient's chest and leaves open the possibility of adding a suction device in later design stages. This assumption was made based on practical considerations and is not expected to influence the strength (i.e., shielding capability) of the shield; and (2) That the respiratory droplets and TEG particles do not significantly alter the airflow. Therefore, one-way coupling is used to describe the drag force between the airflow and the droplets and particles. This assumption is valid because the mass fraction of droplets and particles in the airflow is small.

As described above, the model of FIG. 9 consists of a human head and of a hand holding a tool reaching toward the face originating from the convex side of the shield. It also includes a nozzle that provides the air flow to develop the shield. The model was chosen to mimic typical patient-clinician interaction in a dentistry setting.

Figure 11B:
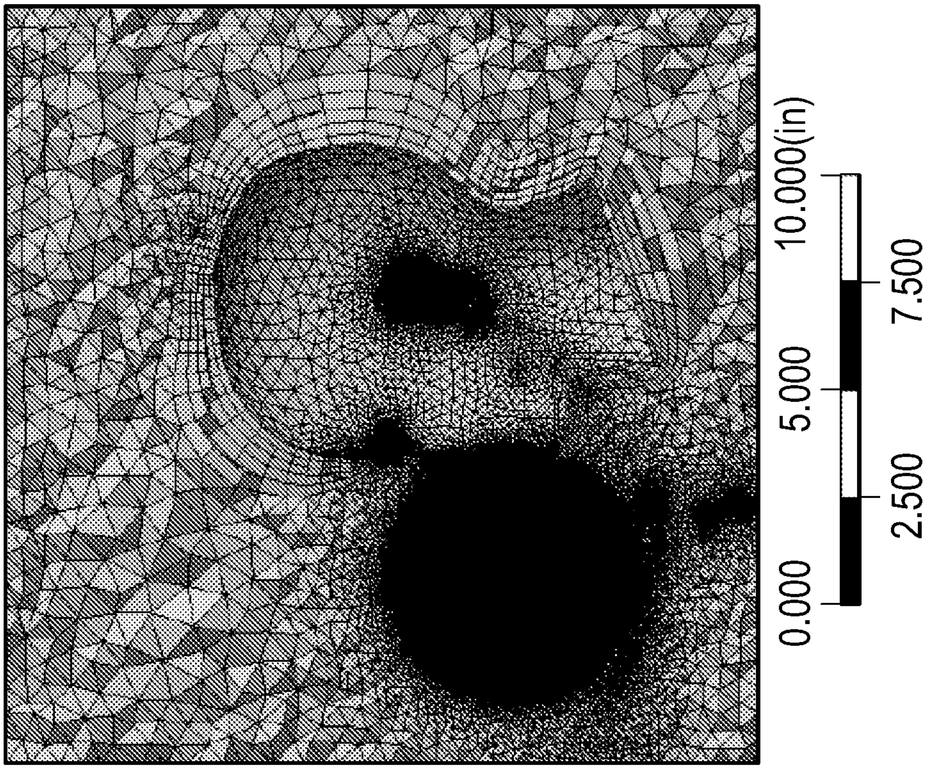
FIG. 11B is a graphic of a refined mesh modeling a head of a patient, according to an exemplary embodiment of the present disclosure.
Figure 11A:
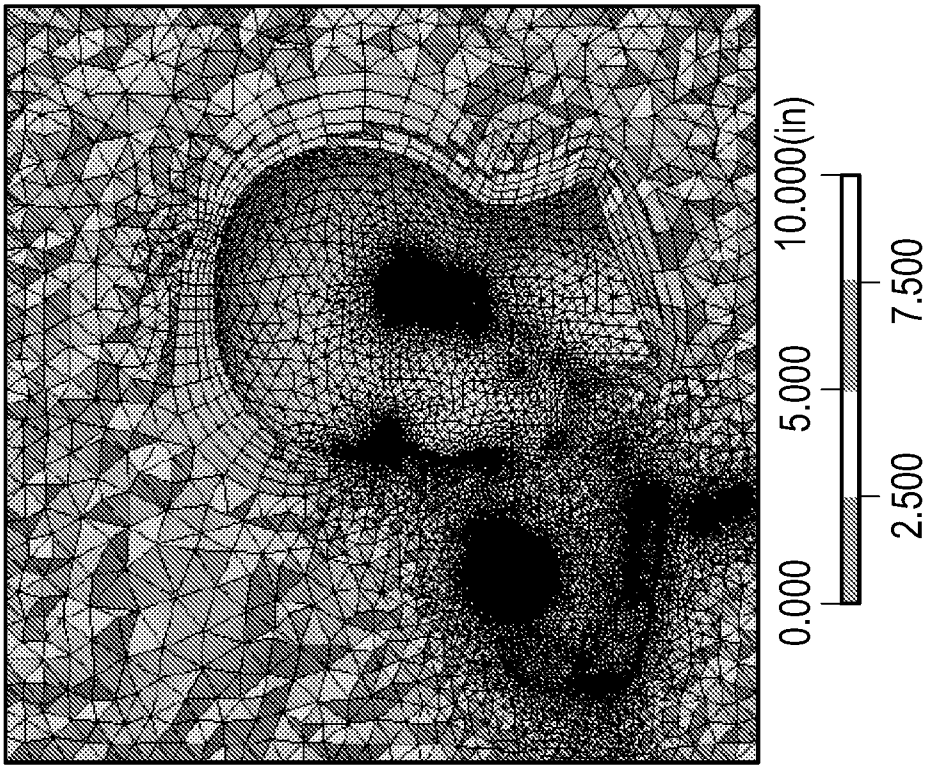
FIG. 11A is a graphic of a mesh modeling a head of a patient, according to an exemplary embodiment of the present disclosure.
Figure 11C:
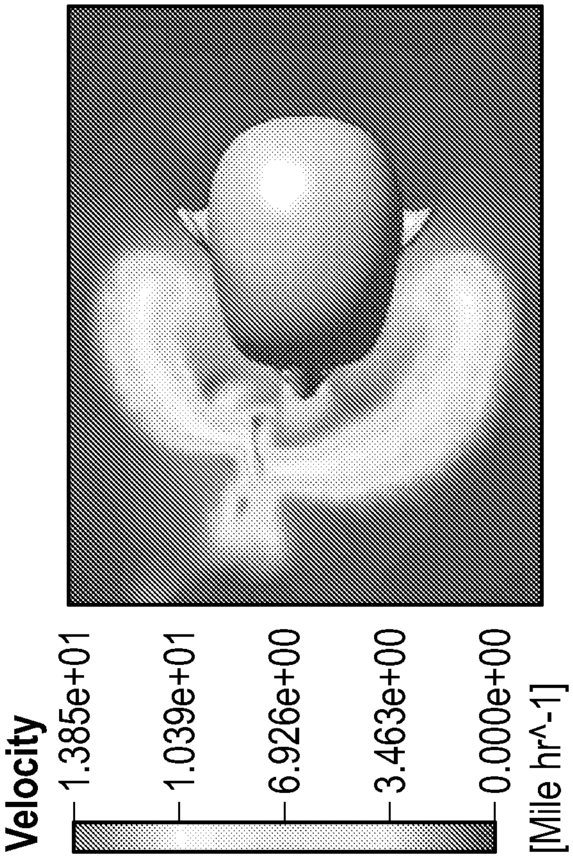
FIG. 11C is a graphic illustrating velocity contours of a mesh modeling a head of a patient, according to an exemplary embodiment of the present disclosure.
Figure 11D:
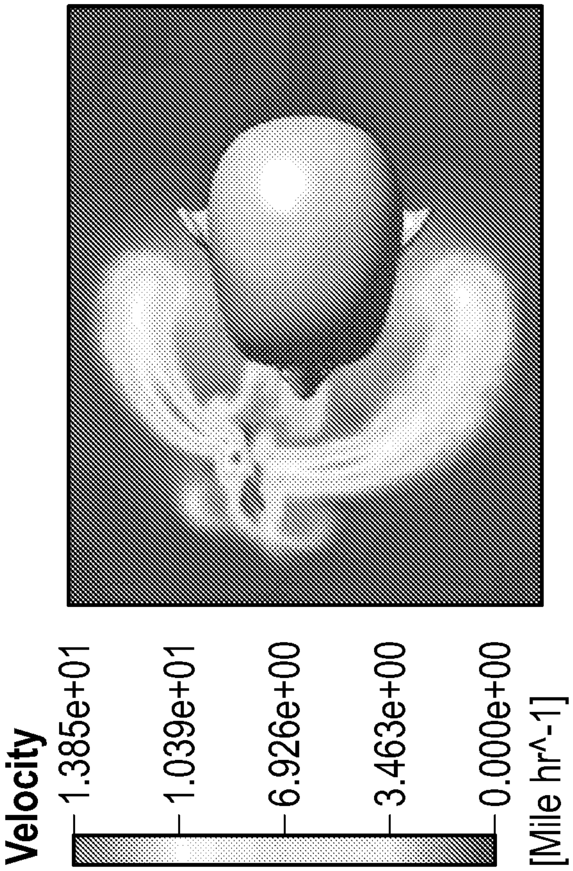
FIG. 11D is a graphic illustrating velocity contours of a mesh modeling a head of a patient, according to an exemplary embodiment of the present disclosure.

To perform subsequent analyses, a mesh must be generated to bridge between the geometry model and the computational model. The mesh is a grid upon which the fluid dynamics equations are solved to obtain velocity and pressure results. Meshing was performed using the ANSYS Workbench Meshing module. The mesh was built with sufficient density in key locations to capture the relevant physics of the process. Inflation layers were added to key surfaces to resolve the flow around these obstacles. Further refinement was added between the hand and face to better resolve the complex flows expected in this region. A second, refined mesh was develop to determine if the first mesh produced sufficiently accurate results. The refined mesh has approximately twice as many nodes as the original mesh. Meshing parameters and selected results for both meshes are provided in Table 2. A side-by-side view of the meshes is shown in FIG. 11A and FIG. 11B. Velocity contour plots for both meshes are shown in FIG. 11C and FIG. 11D. The plots show that the original mesh resolves the flow pattern reasonably well, although there are some localized differences in the peak magnitude of the velocity. Based on the results, it was concluded that the original mesh is sufficiently refined for this feasibility assessment

TABLE 2

| Metric | Unit | Original Mesh | Refined Mesh |
|---|---|---|---|
| Radius of Sphere of Influence | meters | 0.02 | 0.073 |
| Inflation Layer on Lips | — | no | yes |
| Face Sizing on Hand | meters | 0.003 | 0.002 |
| Total Node Count | — | 2,029,814 | 3,953,070 |
| Average Velocity on Vertical Plane | miles per hour | 4.12 | 2.55 |
| Average Velocity on Breath Stream Lines | miles per hour | 2.91 | 3.11 |
| Average Velocity on Stream Lines from Left Inlet | miles per hour | 20.53 | 18.48 |
| Average Velocity on Stream Lines from Right Inlet | miles per hour | 23.68 | 21.98 |

Table 3 summarizes the boundary conditions for the simulation. Note that some boundary conditions change for different cases.

TABLE 3

| Boundary | Parameter | Option | Value |
|---|---|---|---|
| Head, Hand, Tool | Boundary Type | Solid Wall | — |
| | Mass and Momentum | No-Slip | — |
| | Particle Interaction | Coefficient of Restitution | 0 |
| Surrounding Box | Boundary Type | Opening | — |
| | Mass and Momentum | Opening Pressure and Direction | 0 kPa (relative) |
| | Flow Direction | Normal to Boundary | — |
| | Turbulence | Medium Intensity | — |
| Upper Lip | Boundary Type | Inlet | — |
| | Mass and Momentum | Cartesian Velocity Components | u = 1.4 m/s, v = 0 m/s, w = 0 m/s |

TABLE 3-continued

| Boundary | Parameter | Option | Value |
|---|---|---|---|
| | Turbulence | Medium Intensity | — |
| | Particle Injection | Off or On | — |
| | | Material | Water |
| | | Size | 0.3 μm or 10 μm |
| | | Velocity | Zero slip |
| Surrounding Box | Boundary Type | Inlet | — |
| | Mass and Momentum | Cartesian Velocity Components | u = 0 m/s, v = 3 m/s or 15 m/s, w = 0 m/s |
| | Turbulence | Medium Intensity | — |
| | Particle Injection | Off or On | — |
| | | Material | TEG |
| | | Size | 3.72 μm |
| | | Velocity | Zero slip |
| Clinician's Breath (one case only) | Boundary Type | Inlet | — |
| | Mass and Momentum | Cartesian Velocity Components | u = −1.1 m/s, v = −0.5 m/s, w = −0.7 m/s |
| | Turbulence | Medium Intensity | — |
| | Particle Injection | Off or On | — |
| | | Material | Water |
| | | Size | 1 μm |
| | | Velocity | Zero slip |

The simulation involves three materials: air, water droplets, and TEG particles. Air was modeled with constant properties corresponding to a temperature of 25° C. and a pressure of 1 atm. Water and TEG were modeled using a Lagranian approach (i.e., as distinct particles) with one-way coupling to the air flow. For this modeling approach, the density and spherical diameter of the particles are the only parameters of consequence. The droplet and particle diameters for water and TEG are listed in Table 3. Water was modeled with a density of 997 kg/m3. TEG particles were modeled as a mixture of 20 weight percent TEG (density 1125 kg/m3) in water with a mixture density of 1023 kg/m3.

The analysis was performed using ANSYS CFX Version 2020 R1. An overview of the user-selected options in the CFX Preprocessor is given in Table 4.

TABLE 4

| Parameter | Selection | Discussion |
|---|---|---|
| Dimensionality | 3D | The hand and tool make the model non-symmetric. |
| Turbulence Model | SST | The SST model provides good near wall and far field performance. |
| Equation of State | Ideal Gas | In the temperature and pressure range of the simulation, air is considered an ideal gas. |
| Wall Roughness | Smooth | The hand, tool and head were modeled as smooth surfaces. |
| Space Discretization | High Resolution | This scheme provides a blend of first order and higher order schemes to achieve accuracy and boundedness. |
| RMS Residuals | <10-4 | Convergence criteria for RMS residuals of all equations were less than 10-4 |
| Solver Precision | Double | Reduces truncation error |
| | Transient Simulation | |
| Time Discretization | Second Order Backward Euler | Program recommended setting for accuracy |
| Time Step | Adaptive | Time step is adjusted by the solver to achieve a Courant-Friedrich-Levy (CFL) number of <5 |

In the analysis of the cases including particle tracks, the Stokes number is used as an indicator of the particles' ability to follow the bulk flow. A Stokes number above one indicates that the suspended particle is likely to make contact with an obstacle in the flow. The particle would then adhere to the obstacle and, in the case of TEG particles, would be unable to adsorb and capture moisture contained in the breath downstream of the obstacle. A Stokes number less than one indicates that the suspended particle is likely to follow the flow around the obstacle and remain suspended. The Stokes number is calculated according to the following formula:

$$\text{Stokes} = \frac{\rho_p d_p^2 u_0}{18 \mu_0 l_0}$$

where $\rho_p$ is the particle density, $d_p$ is the particle diameter, $u_0$ is the fluid velocity, p is the fluid's dynamic viscosity, and $l_0$ is a characteristic length of the obstacle. A characteristic length of 1 cm was used during post processing to represent the diameter of a likely obstacle such as a tool.

The simulations were performed as outlined above and subsequent analysis and conclusions are summarized below.

Figure 12B:
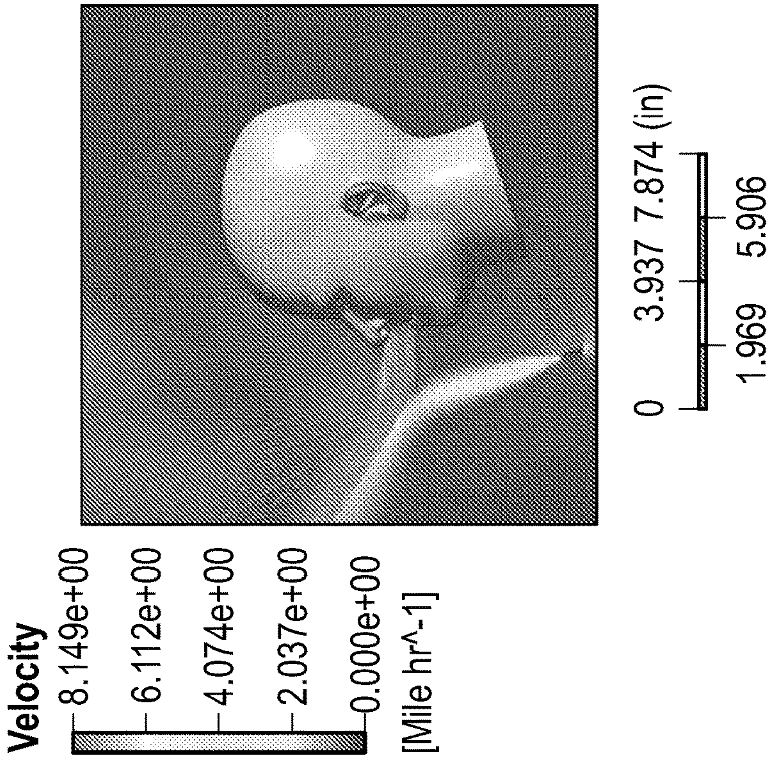
FIG. 12B is a contour plot at a low shield air velocity, according to an exemplary embodiment of the present disclosure.
Figure 12A:
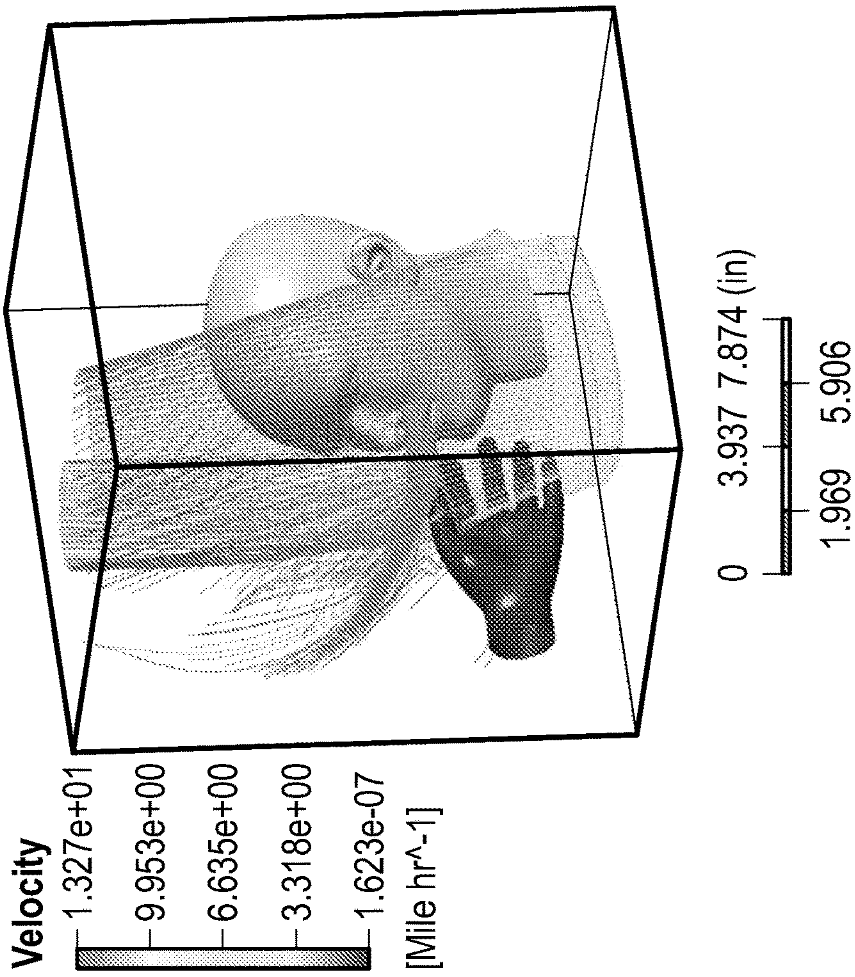
FIG. 12A is a graphic illustrating streamlines at a low shield air velocity, according to an exemplary embodiment of the present disclosure.
Figure 12C:
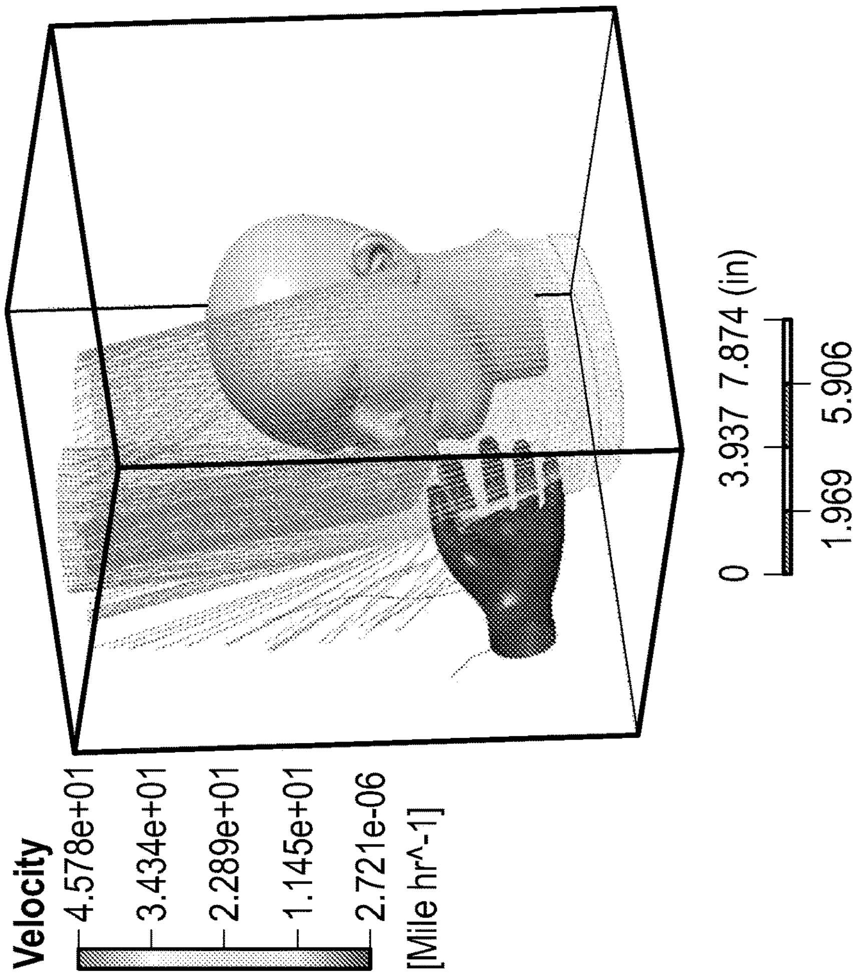
FIG. 12C is a graphic illustrating streamlines at a high shield air velocity, according to an exemplary embodiment of the present disclosure.
Figure 12D:
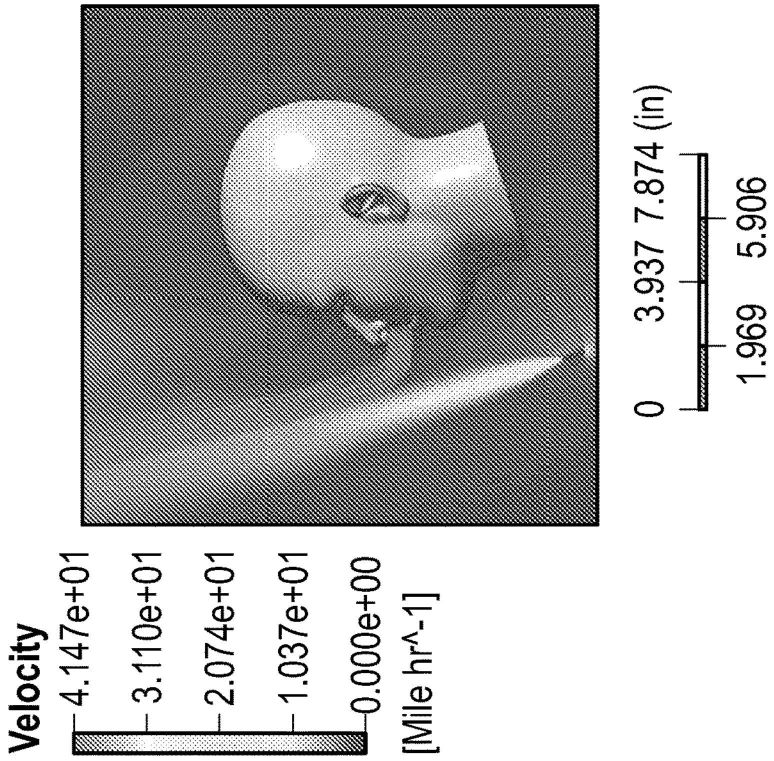
FIG. 12D is a contour plot at a high shield air velocity, according to an exemplary embodiment of the present disclosure.
Figure 12E:
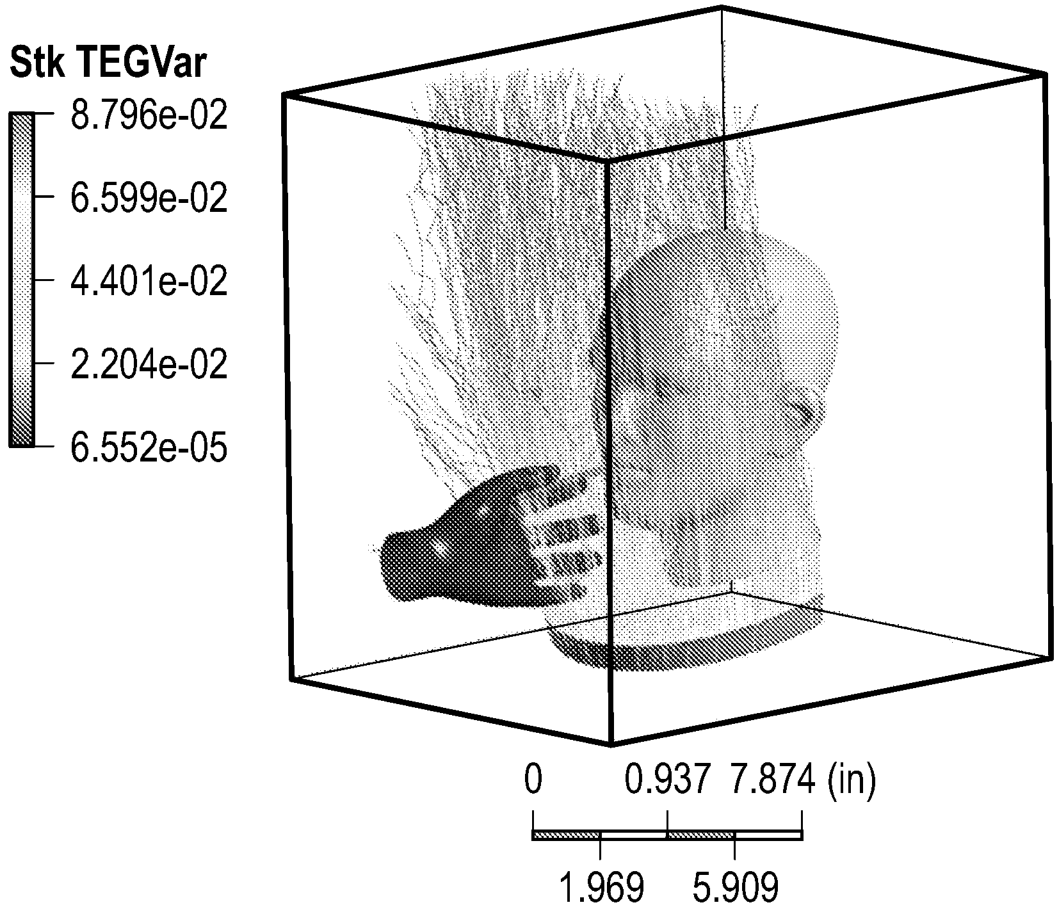
FIG. 12E is a graphic illustrating particle tracks of triethylene glycol particles, according to an exemplary embodiment of the present disclosure.
Figure 12F:
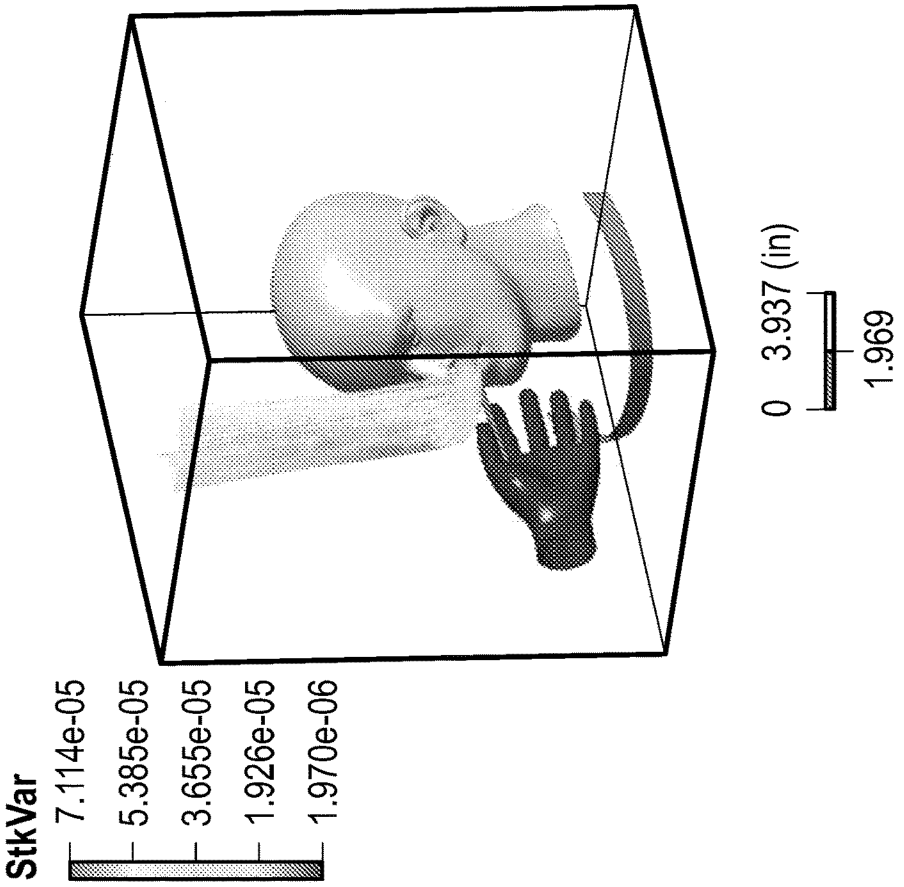
FIG. 12F is a graphic illustrating particle tracks of small water droplets, according to an exemplary embodiment of the present disclosure.
Figure 12G:
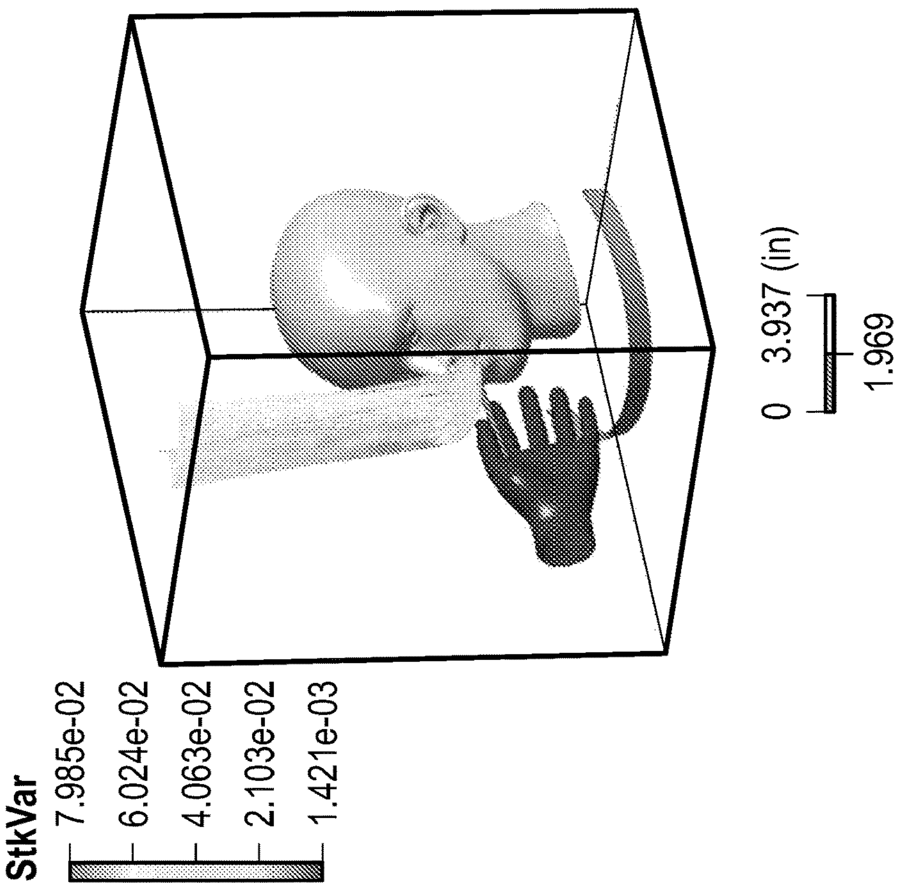
FIG. 12G is a graphic illustrating particle tracks of large water droplets, according to an exemplary embodiment of the present disclosure.

As described above, the person on the concave side of the shield is referred to as the patient, while the person on the convex side of the shield is referred to as the clinician. This choice of terminology is arbitrary and does not impact the results or conclusions. FIG. 12A and FIG. 12B show the results of the simulation at low shield air speed (A1B1). FIG. 12A shows streamlines from the air nozzle colored by velocity, and streamlines from the patient's mouth in grey. FIG. 12B shows a contour plot of velocity overlaid with streamlines starting at the patient's mouth. In both images, blue indicates low velocities and red indicates high velocities. Both plots show that the air velocity is insufficient to create a shield and the breath of a user is not diverted effectively. FIG. 12C and FIG. 12D show the results of the simulation at high shield air speed (A2B1). As before, blue indicates low velocities and red indicates high velocities. In this case, the air velocity is high enough to separate a user's breath within the shield. Similar results are obtained from the simulation using a wide slit (A2B2). FIG. 12E through FIG. 12G show the results of a simulation including TEG particles in the airstream and water droplets in a user's breath (A2B1C2 and A2B1D1/23). The lines shown in the Figures are tracks that trace the path of representative particles. As opposed to streamlines, which trace hypothetical massless particles, particle tracks follow finite-sized particles with mass. The lines are colored by the Stokes number which is a measure of the suspended particle's ability to follow the bulk flow. A Stokes number above one indicates that the suspended particle is likely to make contact with an obstacle in the flow. The particle would then adhere to the obstacle and, in the case of TEG particles, would be unable to adsorb and capture moisture contained in the breath downstream of the obstacle. A Stokes number less than one indicates that the suspended particle will follow the flow around the obstacle and remain suspended. A mathematical definition of the Stokes number is provided above. The Stokes numbers for all cases are significantly less than one indicating that the droplets and TEG particles are well entrained in the flow. Note that the color patterns on the particle tracks for the respiratory droplets in FIG. 12F and FIG. 12G are similar in appearance but different in magnitude. The difference in magnitude is due to the different size (0.3 μm vs. 10 μm) of the droplets in FIG. 12F and FIG. 12G, respectively. In general, the smaller droplets resulted in smaller Stokes numbers compared to the larger droplets, indicating the smaller droplets will entrain in the airstream more easily than the larger droplets, although both the small and large droplets were sufficiently entrained in the airstream.

Figure 12H:
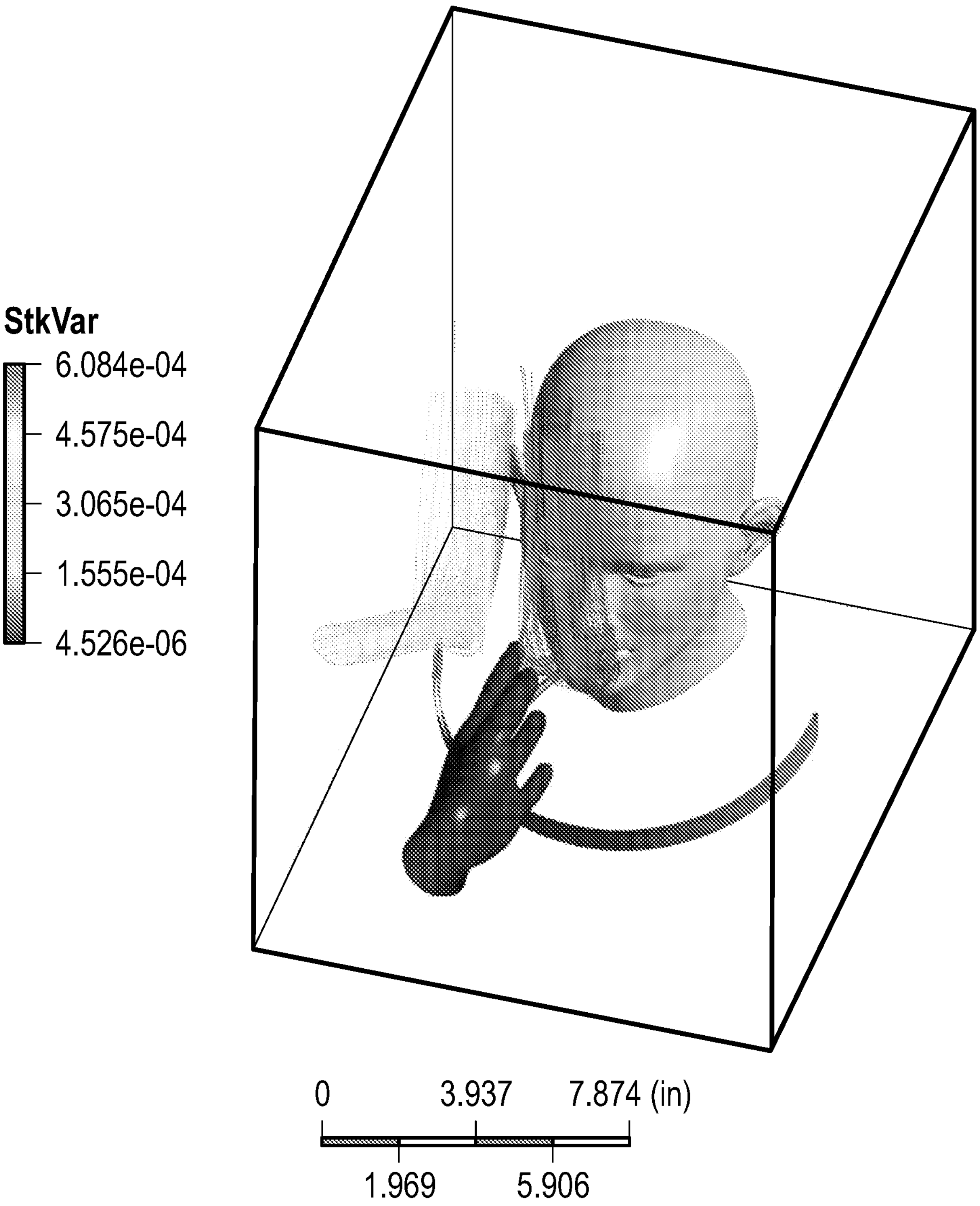
FIG. 12H is a graphic illustrating particle tracks of water droplets with a breath stream from outside the shield, according to an exemplary embodiment of the present disclosure.
Figure 12I:
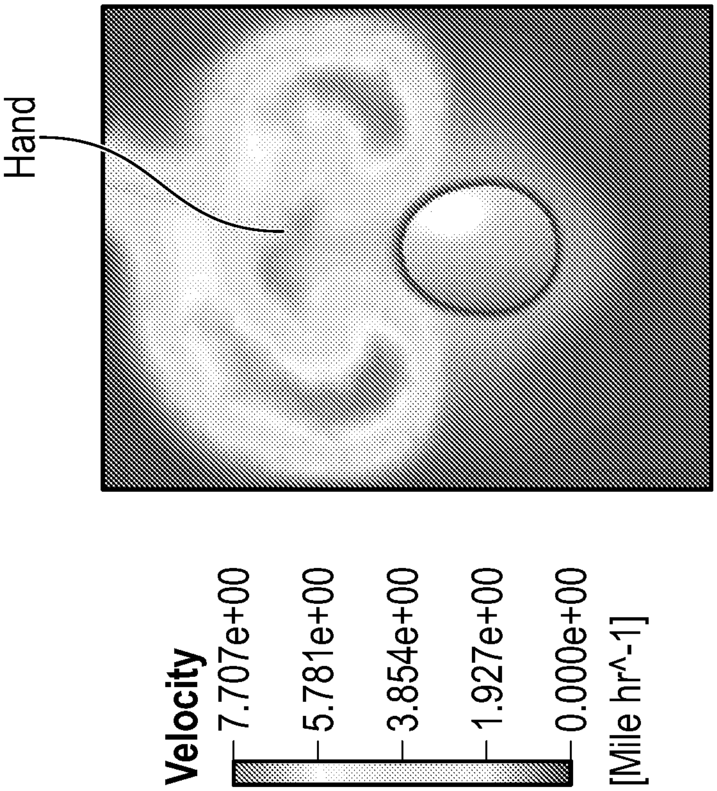
FIG. 12I is a graphic illustrating a top view of velocity contours without a breath stream from outside the shield, according to an exemplary embodiment of the present disclosure.
Figure 12J:
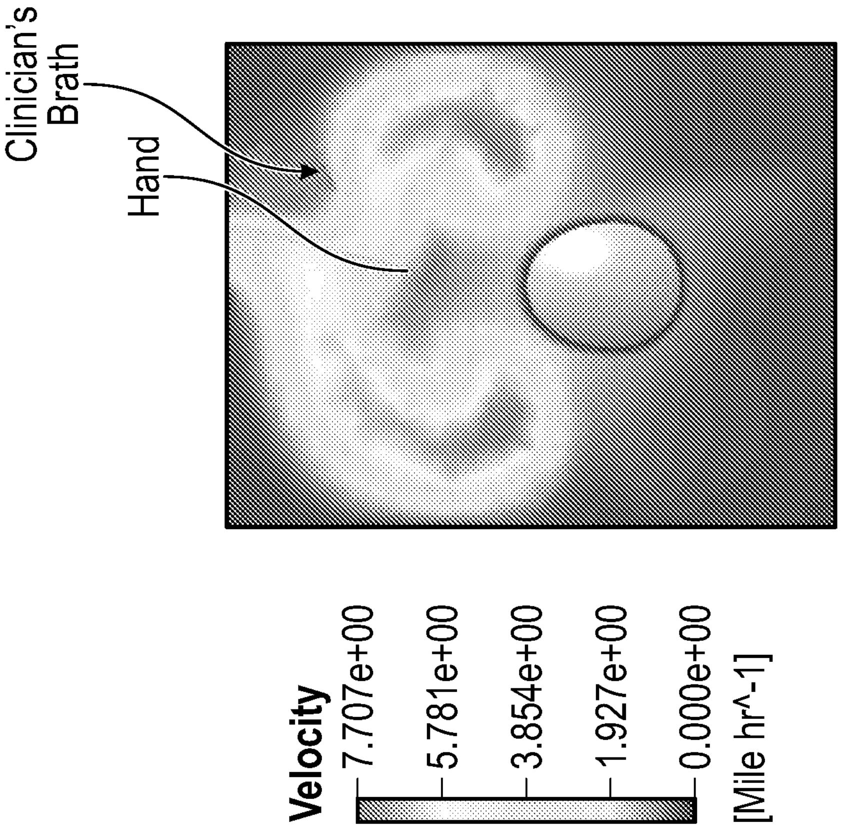
FIG. 12J is a graphic illustrating a top view of velocity contours with a breath stream from outside the shield, according to an exemplary embodiment of the present disclosure.
Figure 13A:
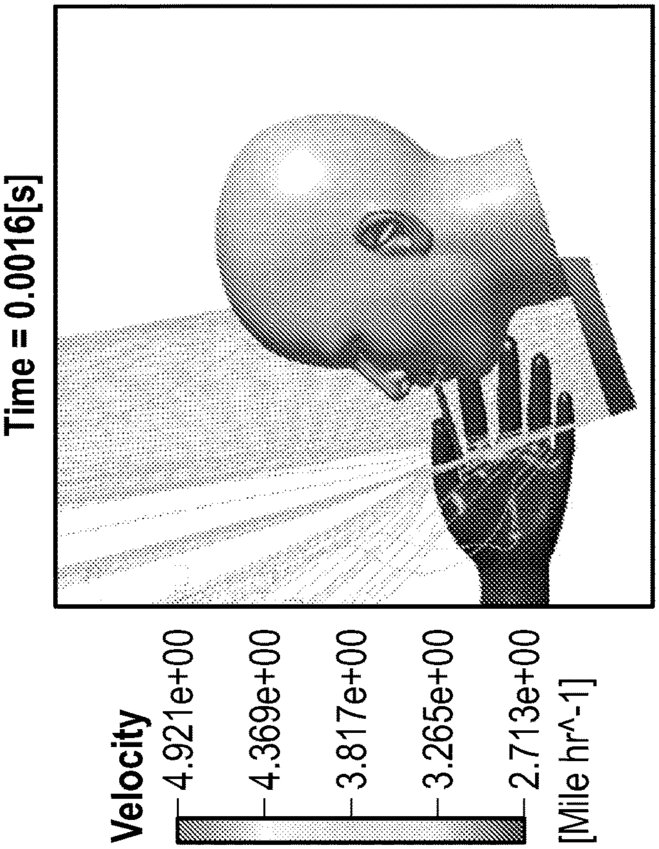
FIG. 13A is a graphic illustrating air streamlines and breath droplet tracks for a weak cough during a given time segment, according to an exemplary embodiment of the present disclosure.
Figure 13B:
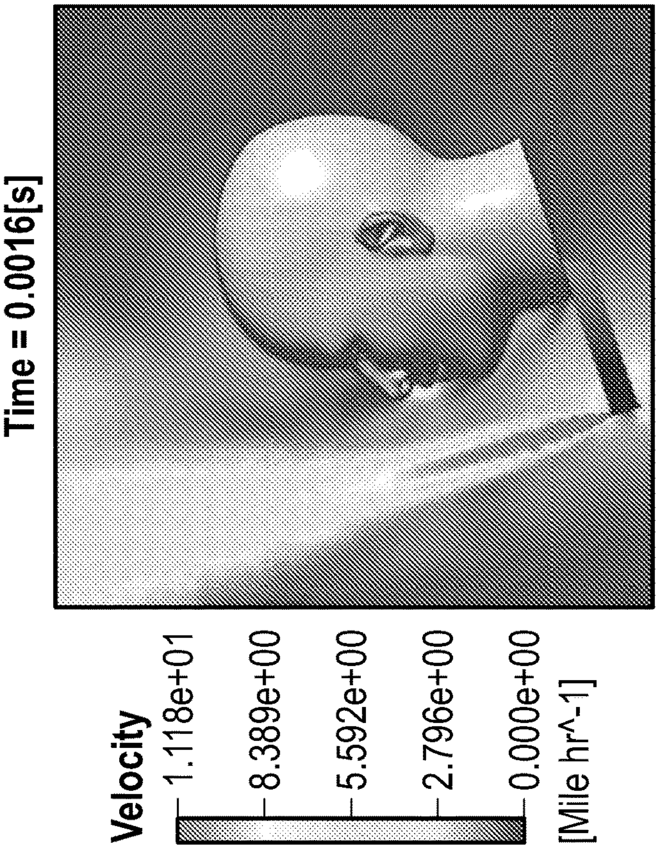
FIG. 13B is a graphic illustrating velocity contours for a weak cough during a given time segment, according to an exemplary embodiment of the present disclosure.
Figure 13C:
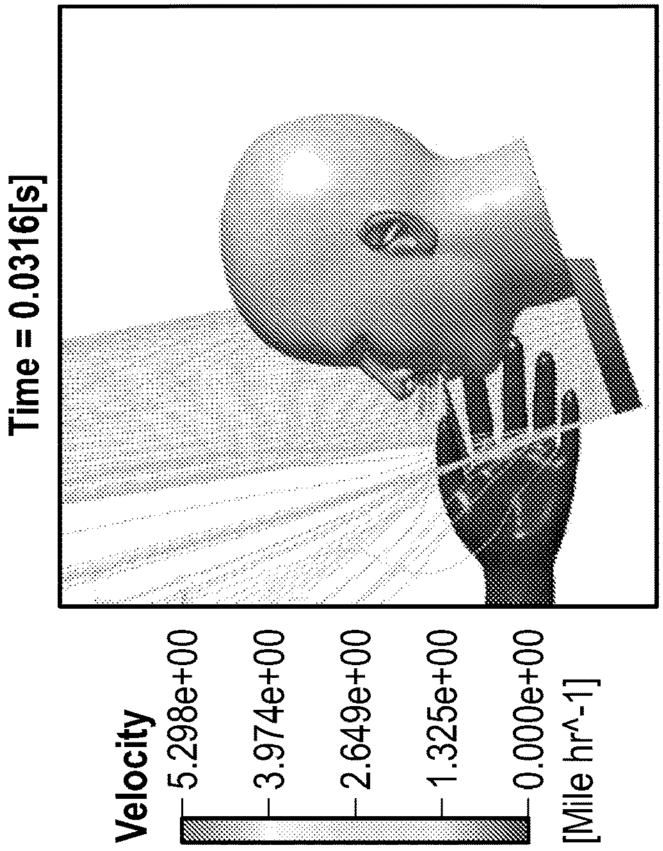
FIG. 13C is a graphic illustrating air streamlines and breath droplet tracks for a weak cough during a given time segment, according to an exemplary embodiment of the present disclosure.
Figure 13D:
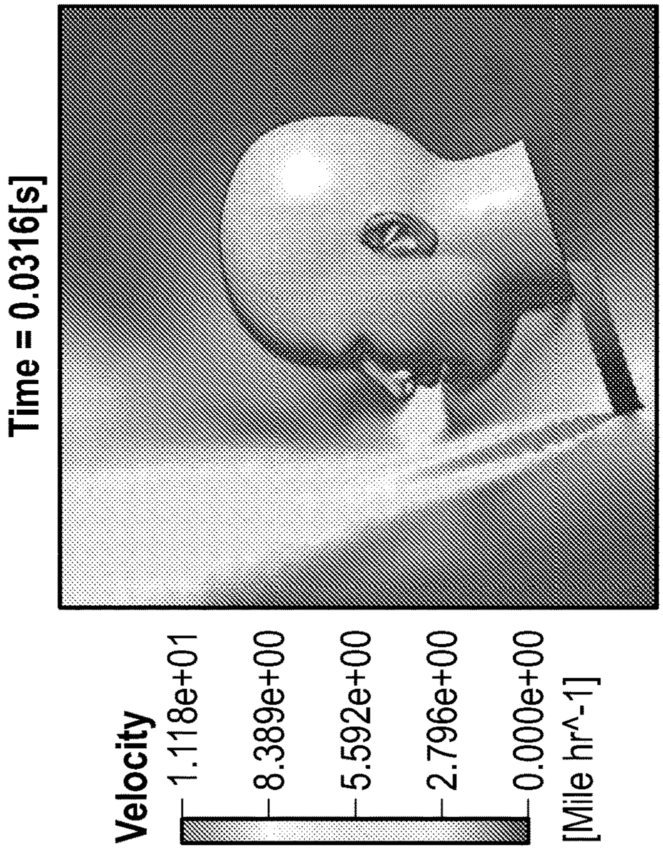
FIG. 13D is a graphic illustrating velocity contours for a weak cough during a given time segment, according to an exemplary embodiment of the present disclosure.
Figure 13E:
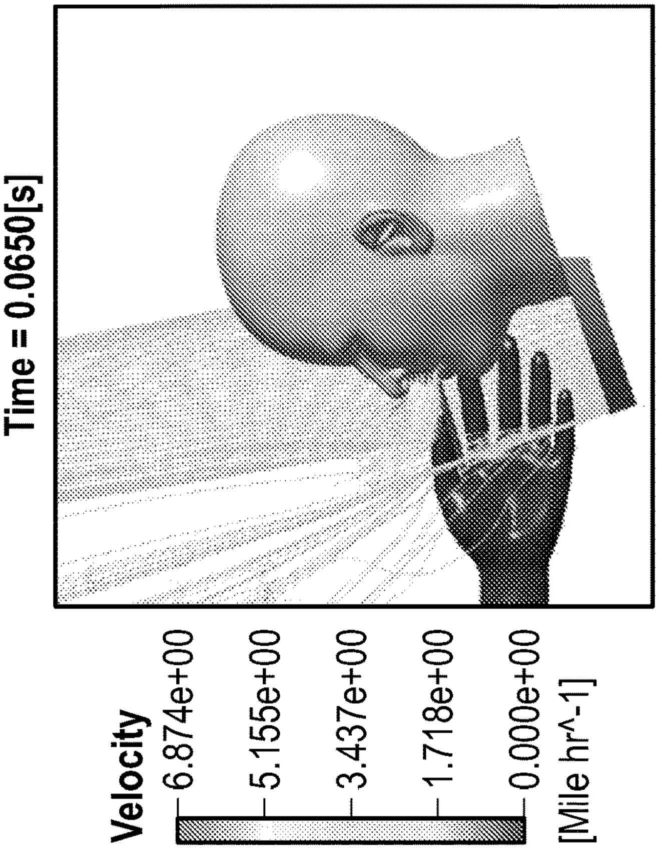
FIG. 13E is a graphic illustrating air streamlines and breath droplet tracks for a weak cough during a given time segment, according to an exemplary embodiment of the present disclosure.
Figure 13F:
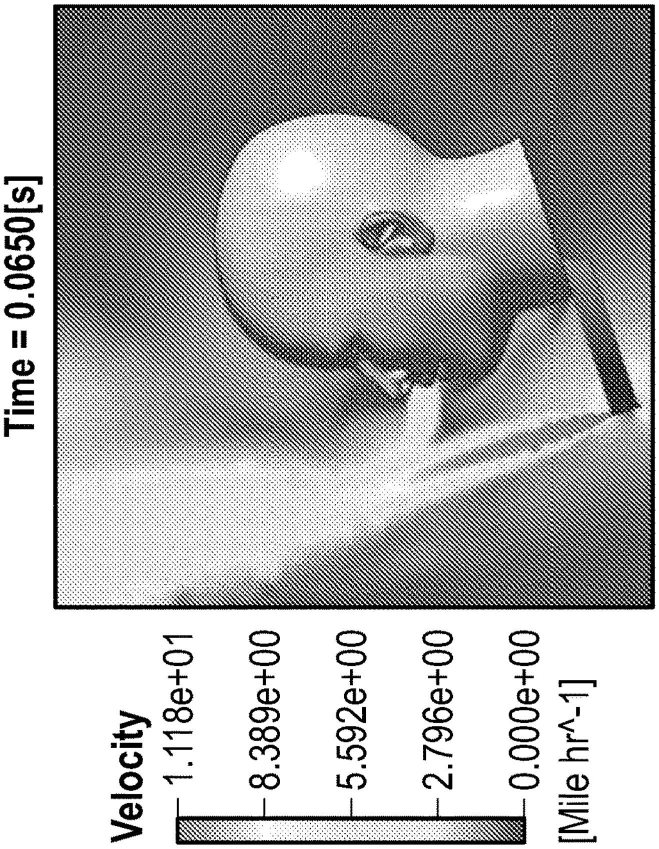
FIG. 13F is a graphic illustrating velocity contours for a weak cough during a given time segment, according to an exemplary embodiment of the present disclosure.
Figure 13G:
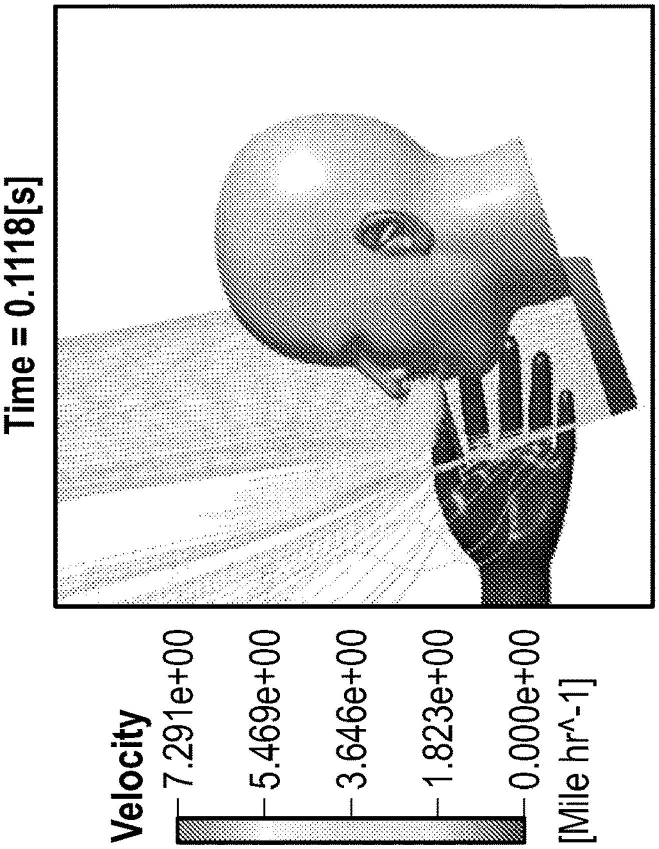
FIG. 13G is a graphic illustrating air streamlines and breath droplet tracks for a weak cough during a given time segment, according to an exemplary embodiment of the present disclosure.
Figure 13H:
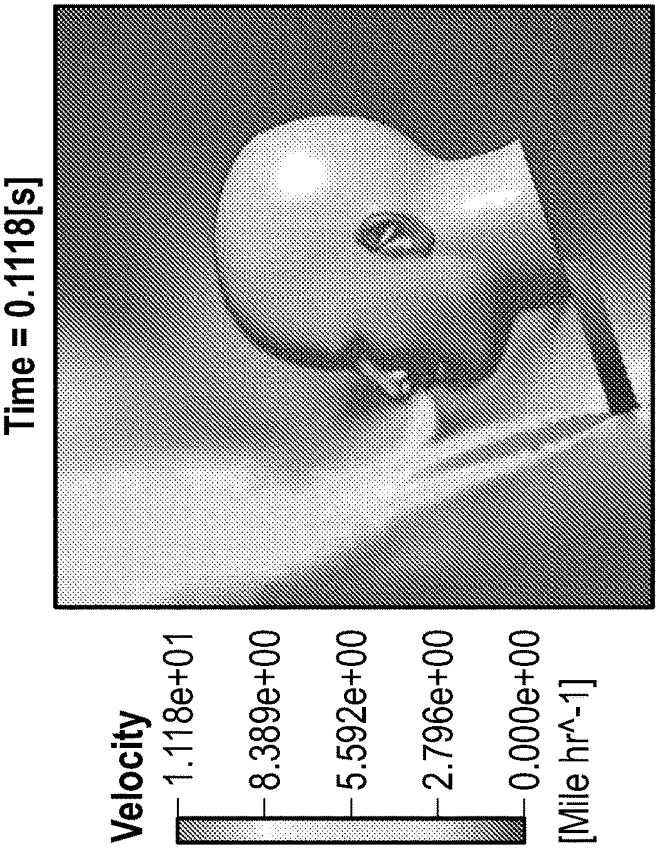
FIG. 13H is a graphic illustrating velocity contours for a weak cough during a given time segment, according to an exemplary embodiment of the present disclosure.
Figure 13I:
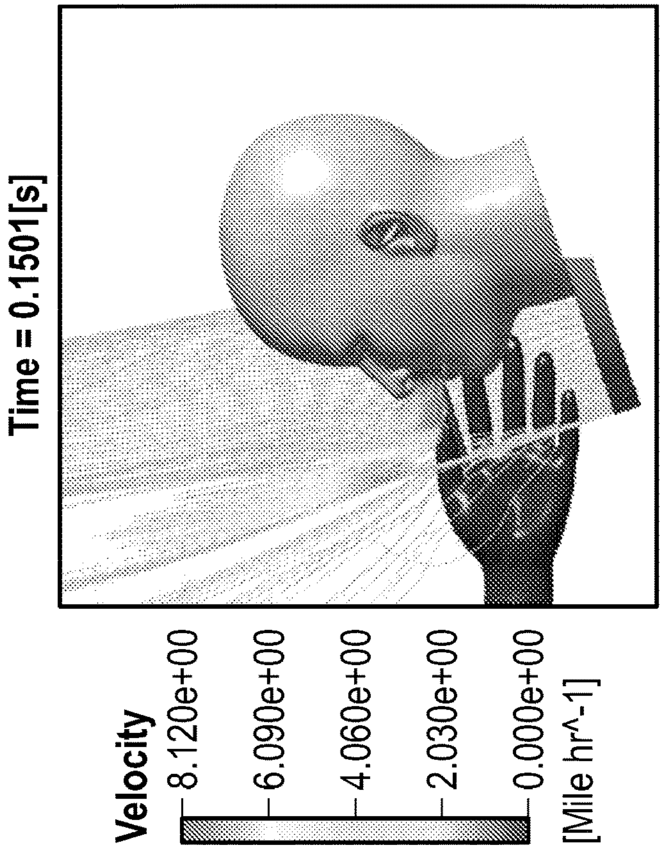
FIG. 13I is a graphic illustrating air streamlines and breath droplet tracks for a weak cough during a given time segment, according to an exemplary embodiment of the present disclosure.
Figure 13J:
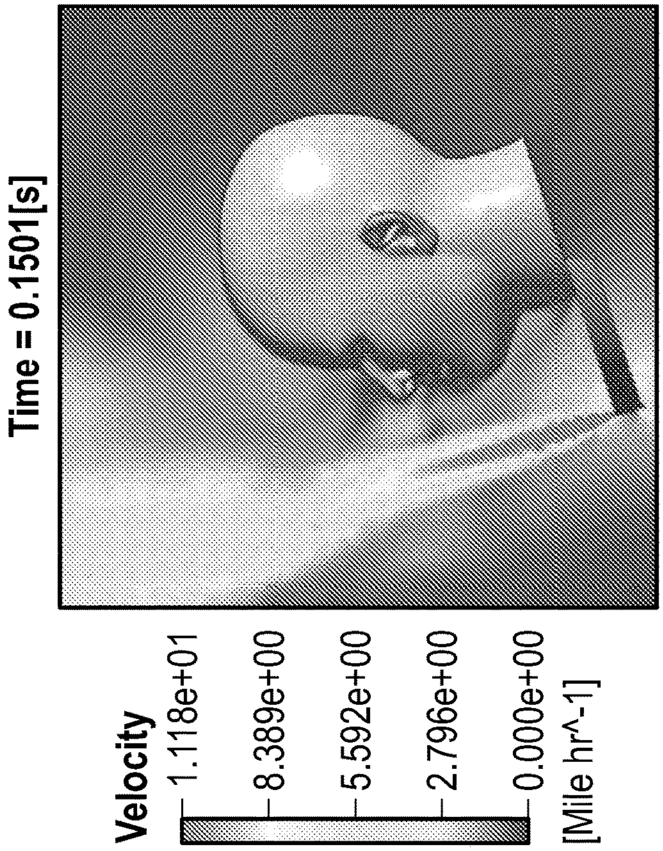
FIG. 13J is a graphic illustrating velocity contours for a weak cough during a given time segment, according to an exemplary embodiment of the present disclosure.
Figure 14A:
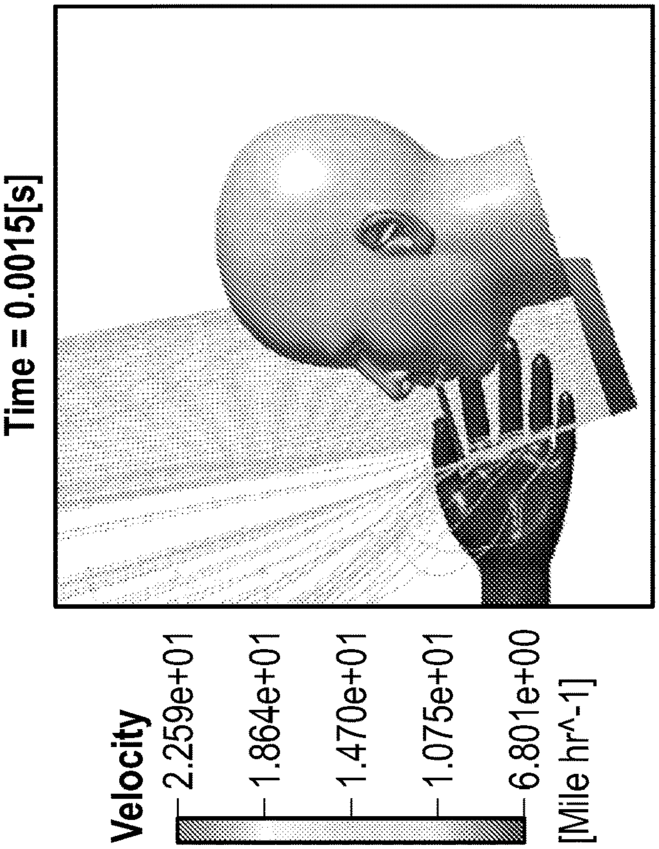
FIG. 14A is a graphic illustrating air streamlines and breath droplet tracks for a strong cough during a given time segment, according to an exemplary embodiment of the present disclosure.
Figure 14B:
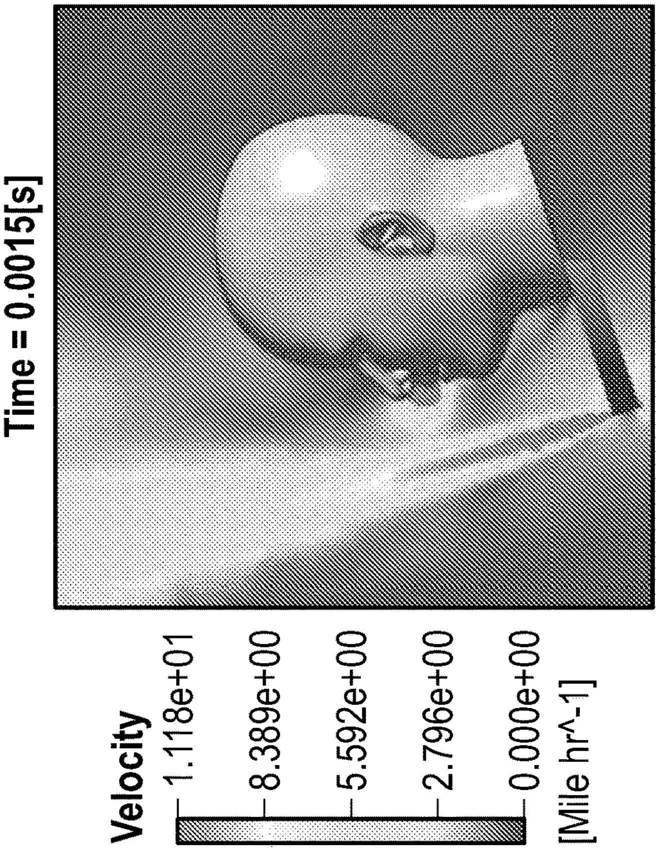
FIG. 14B is a graphic illustrating velocity contours for a strong cough during a given time segment, according to an exemplary embodiment of the present disclosure.
Figure 14C:
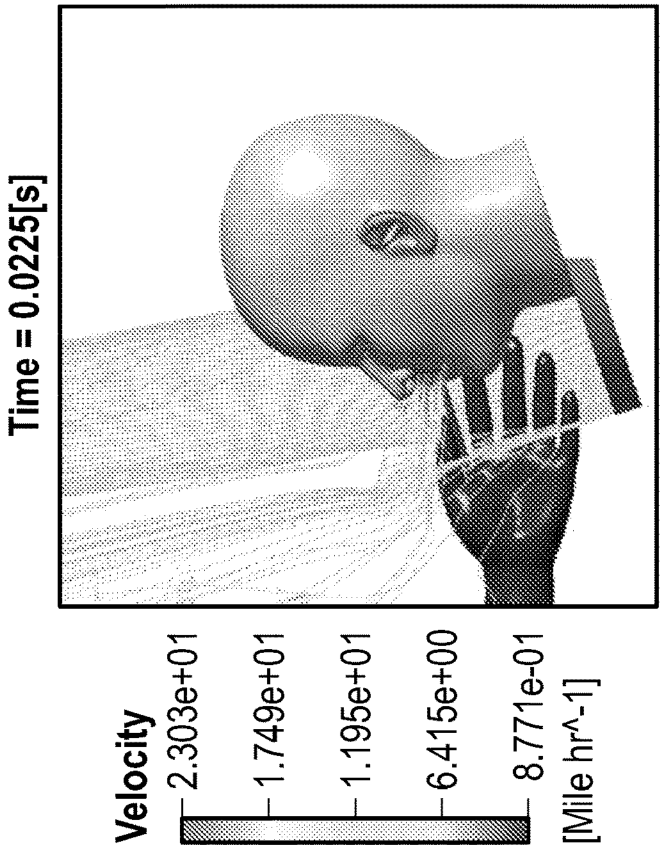
FIG. 14C is a graphic illustrating air streamlines and breath droplet tracks for a strong cough during a given time segment, according to an exemplary embodiment of the present disclosure.
Figure 14D:
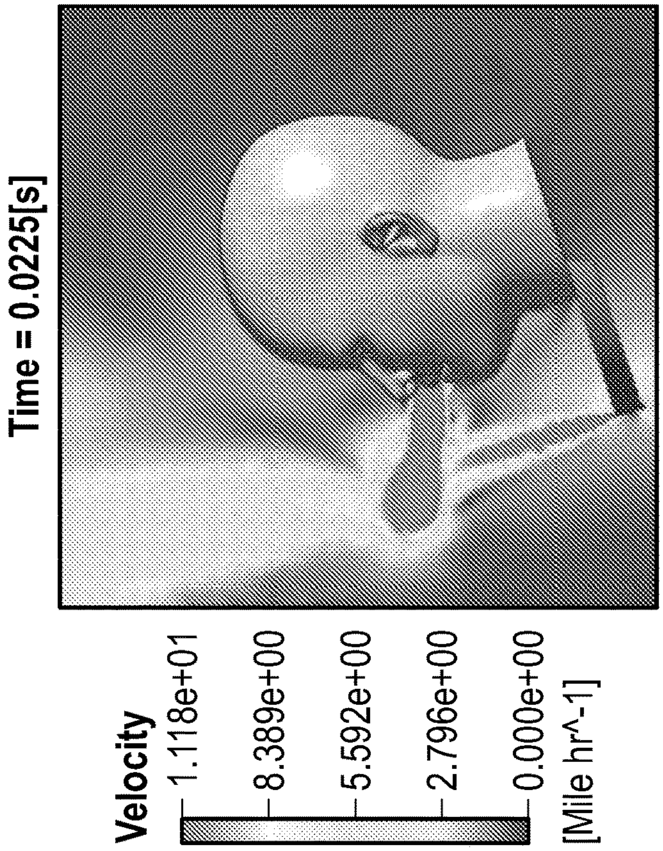
FIG. 14D is a graphic illustrating velocity contours for a strong cough during a given time segment, according to an exemplary embodiment of the present disclosure.
Figure 14E:
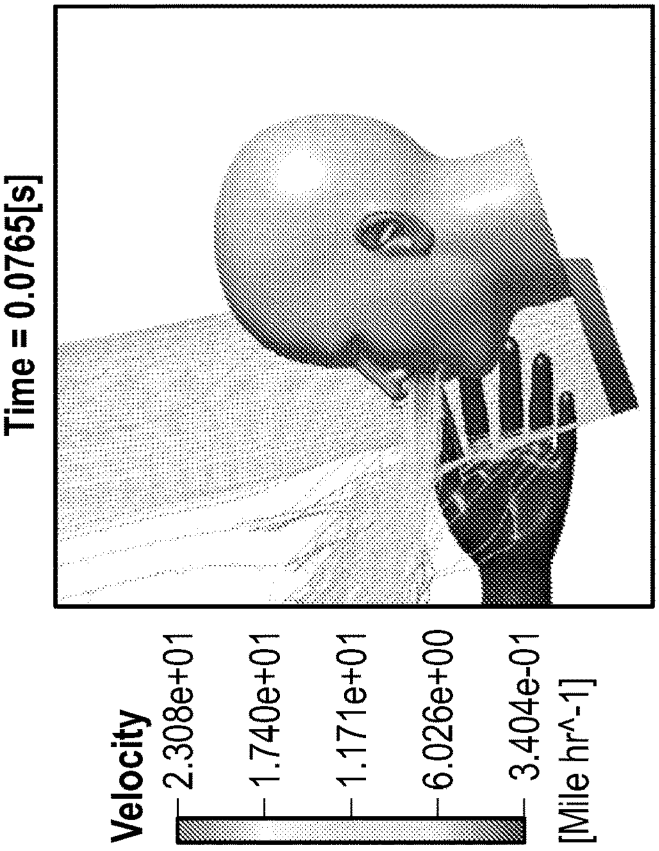
FIG. 14E is a graphic illustrating air streamlines and breath droplet tracks for a strong cough during a given time segment, according to an exemplary embodiment of the present disclosure.
Figure 14F:
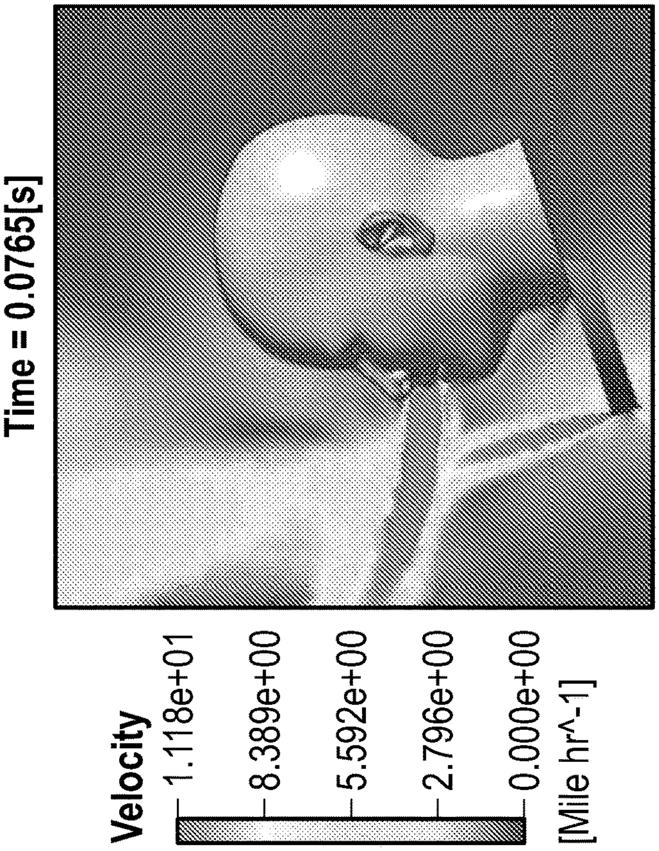
FIG. 14F is a graphic illustrating velocity contours for a strong cough during a given time segment, according to an exemplary embodiment of the present disclosure.
Figure 14G:
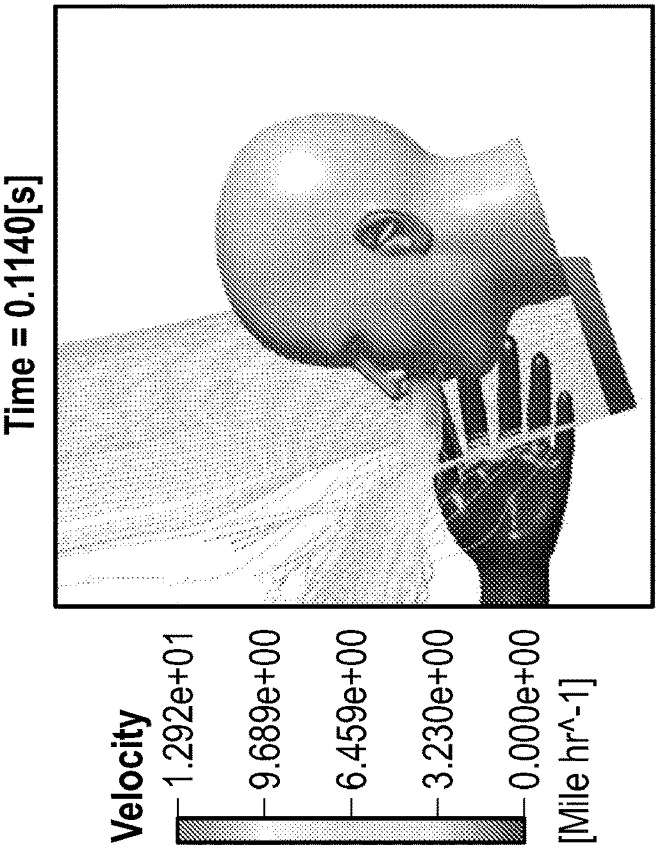
FIG. 14G is a graphic illustrating air streamlines and breath droplet tracks for a strong cough during a given time segment, according to an exemplary embodiment of the present disclosure.
Figure 14H:
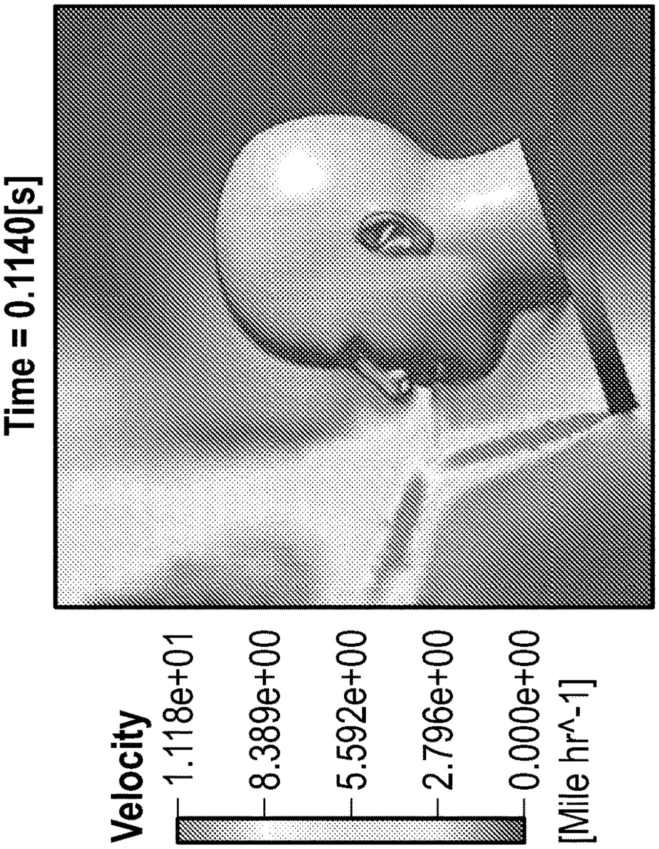
FIG. 14H is a graphic illustrating velocity contours for a strong cough during a given time segment, according to an exemplary embodiment of the present disclosure.
Figure 14I:
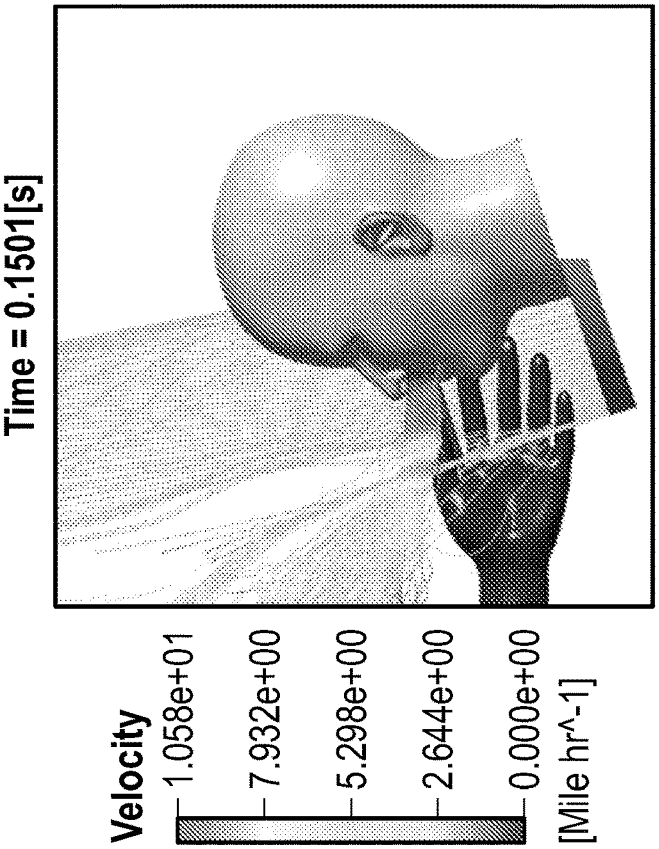
FIG. 14I is a graphic illustrating air streamlines and breath droplet tracks for a strong cough during a given time segment, according to an exemplary embodiment of the present disclosure.
Figure 14J:
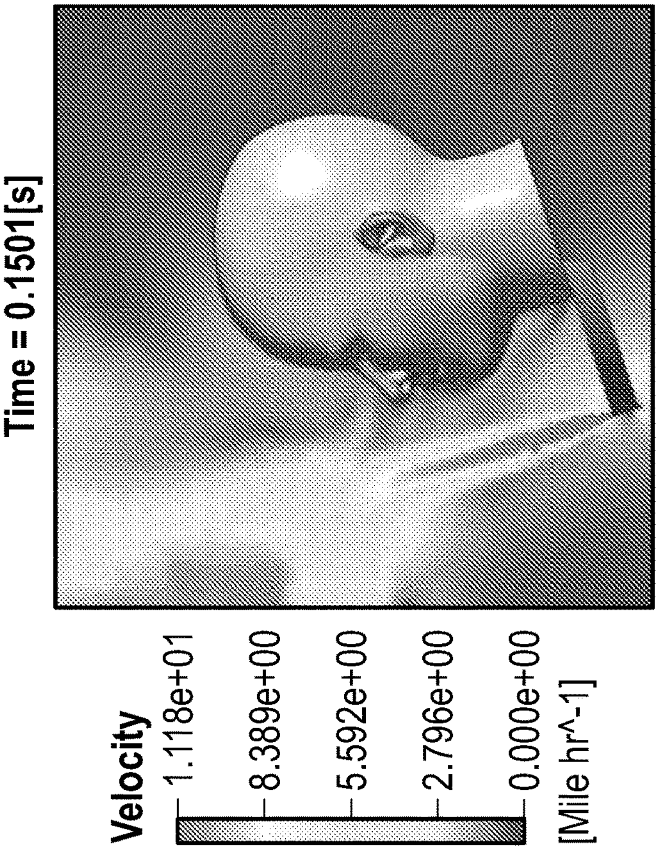
FIG. 14J is a graphic illustrating velocity contours for a strong cough during a given time segment, according to an exemplary embodiment of the present disclosure.

FIG. 12H through FIG. 12J show the results from the simulation including a breath stream outside the fluidic shield (A2B1C2D1E1) in addition to the normal breathing of the user on the concave side of the shield. The particle tracks for the respiratory droplets show that the breath streams from both parties are effectively separated by the fluidic shield (FIG. 12H). The droplets released from the user's mouth on the concave side of the shield (patient) are smaller than those released by the person on the convex side of the shield (clinician), and therefore, the Stokes number for the patient's breath droplets are lower. However, the Stokes number for both streams indicate good entrainment (i.e., Stokes number<<1). Different droplet sizes were used for patient and clinician to confirm that droplets of either size can be deflected by the shield flow. The size of both droplets is within the range identified through experiments. In FIG. 12I and FIG. 12J, the black lines show the approximate location of the clinician's hand penetrating the shield and slightly reducing the shield's velocity. The red arrow indicates the approximate direction of the clinician's breath, which causes a small deformation of the shield but does not lead to breakdown of the shield integrity.

FIG. 13A through FIG. 13J show the transient evolution of a weak cough (2.2 m/s, 4.9 mph). The cough pulse starts at 0 seconds from a steady-state flow field of the shield in which the patient does not exhale, and ends after 0.1 seconds. FIG. 13A, FIG. 13C, FIG. 13E, FIG. 13G, and FIG. 13I illustrate grey-colored streamlines starting from the inlet nozzle of the collar, and respiratory droplet tracks colored by velocity starting from the patient's mouth. Note that the droplet size used is for normal breathing and that the size of droplets expelled through a cough may vary. FIG. 13B, FIG. 13D, FIG. 13F, FIG. 13H, and FIG. 13J illustrate velocity contours for the same period. The cough slightly deforms the fluidic shield but does not break through the shield. FIG. 14A through FIG. 14J show similar images for a strong cough (10 m/s, 22.4 mph). In this case, the cough and shield velocities are similar in magnitude and the cough has sufficient momentum to break through the shield. After the cough has passed, the fluidic shield is reestablished by the airflow from the collar.

The computation fluid dynamics simulations and parametric study support the following conclusions. First, the fluidic shield concept is feasible. In the investigated configuration, a shield with an initial air velocity of 15 m/s (33.6 mph) at the source is capable of deflecting the user's breath for a range of scenarios and operating conditions, including a weak cough carrying respiratory droplets. At the point of interaction the velocity of the shield air and breath are approximately 4 m/s (9 mph) and 1.1 m/s (2.5 mph), respectively, for A2B1. Next, the shield is capable of redirecting/deflecting moisture droplets carried in the breath from either side of the shield making it effective for the patient and clinician. Interference from the hand and tool leads to a minor disruption of the shield but does not cause a breakdown. However, other hand positions, or multiple hands in the airstream, were not investigated and could lead to a larger disruption in the shield that may lead to a breakdown in confinement. These types of situations should be studied in a future analysis in conjunction with a human factors study. The fluidic shield is able to transport TEG particles to provide additional protection against transmission between the patient and clinician. This may be beneficial in cases where the shield is disrupted due to obstacles and there is a higher degree of mixing between breath and shield air flows. The shield is challenged when the cough velocity approaches the velocity of the shield air.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) A system for removing pathogens from a dental operatory, comprising a manifold in fluid connection with a fluid source, the manifold including a plurality of apertures for directing a fluid stream, a fluid pump for pressurizing a fluid within the fluid source, and processing circuitry configured to instruct the fluid pump to pressurize the fluid, and instruct the fluid pump to pump the pressurized fluid to the manifold such that the directed fluid stream generates a fluid shield relative to an object.

(2) The system of (1), wherein the pressurized fluid is water or air.

(3) The system of either (1) or (2), further comprising a reservoir containing at least a disinfectant, the processing circuitry being further configured to instruct mixing of the disinfectant with the pressurized fluid pumped to the manifold.

(4) The system of any one of (1) to (3), wherein the disinfectant is mixed with the pressurized fluid at a concentration of between 0.5% and 20%.

(5) The system of any one of (1) to (4), wherein the disinfectant includes triethylene glycol particles.

(6) The system of any one of (1) to (5), wherein the triethylene glycol particles are between 1.26 μm and 3.72 μm.

(7) The system of any one of (1) to (6), wherein the manifold has a substantially-arced shape, the fluid stream directed therefrom forming a semi-cylindrical fluid column.

(8) The system of any one of (1) to (7), further comprising a vacuum, the processing circuitry being further configured to instruct the vacuum to evacuate the directed fluid stream from the dental operatory.

(9) The system of any one of (1) to (8), wherein the plurality of apertures have a diameter of between 3 mm and 6 mm.

(10) An apparatus for removing pathogens from a dental operatory, comprising a manifold in fluid connection with a fluid source, the manifold including a plurality of apertures for directing a fluid stream, a fluid pump for pressurizing a fluid within the fluid source, and processing circuitry configured to instruct the fluid pump to pressurize the fluid, and instruct the fluid pump to pump the pressurized fluid to the manifold such that the directed fluid stream generates a fluid shield relative to an object.

(11) The apparatus of (10), wherein the pressurized fluid is water or air.

(12) The apparatus of either (10) or (11), further comprising a reservoir containing at least a disinfectant, the processing circuitry being further configured to instruct mixing of the disinfectant with the pressurized fluid pumped to the manifold.

(13) The apparatus of any one of (10) to (12), wherein the disinfectant includes triethylene glycol particles.

(14) The apparatus of any one of (10) to (13), wherein the triethylene glycol particles are between 1.26 μm and 3.72 μm.

(15) The apparatus of any one of (10) to (14), wherein the manifold has a substantially-arced shape, the fluid stream directed therefrom forming a semi-cylindrical fluid column.

(16) The apparatus of any one of (10) to (15), wherein the plurality of apertures have a diameter of between 3 mm and 6 mm.

(17) A system for removing pathogens, comprising a manifold in fluid connection with a fluid source, the manifold including a plurality of apertures for directing a fluid stream, a fluid pump for pressurizing a fluid within the fluid source, and processing circuitry configured to instruct the fluid pump to pressurize the fluid, and instruct the fluid pump to pump the pressurized fluid to the manifold such that the directed fluid stream generates a fluid shield relative to an object.

(18) The system of (17), wherein the pressurized fluid is water or air.

(19) The system of either (17) or (18), further comprising a reservoir containing at least a disinfectant, the processing circuitry being further configured to instruct mixing of the disinfectant with the pressurized fluid pumped to the manifold.

(20) The system of any one of (17) to (19), further comprising a vacuum, the processing circuitry being further configured to instruct the vacuum to evacuate the directed fluid stream.

(21) A method for removing pathogens from a dental operatory, comprising instructing, by processing circuitry, a fluid pump to pressurize a fluid within a fluid source that is in fluid connection with a manifold, the manifold including a plurality of apertures for directing a fluid stream, and instructing, by the processing circuitry, the fluid pump to pump the pressurized fluid to the manifold such that the directed fluid stream generates a fluid shield relative to an object.

(22) The method of (21), further comprising providing, by the processing circuitry, a disinfectant with the pressurized fluid pumped to the manifold, the disinfectant including triethylene glycol particles of between 1.26 μm and 3.72 μm.

(23) The method of either (21) or (22), wherein an exit velocity of the fluid stream being directed from the plurality of apertures of the manifold is between 3 m/s and 15 m/s.

(24) The method of any one of (21) to (23), further comprising removing, by the processing circuitry, the directed fluid stream from the dental operatory via activation of a vacuum source.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A system for removing pathogens from a dental operatory, comprising:

a manifold in fluid connection with a fluid source, the manifold including a plurality of apertures for directing a fluid stream, a reservoir containing at least a bioaerosol particle entrainer, a fluid pump for pressurizing a fluid within the fluid source, and processing circuitry configured to instruct the fluid pump to pressurize the fluid, instruct the fluid pump to pump the pressurized fluid to the manifold such that the directed fluid stream generates a fluid shield relative to an object, and instruct mixing of the bioaerosol particle entrainer with the pressurized fluid pumped to the manifold such that the bioaerosol particle entrainer is introduced into the fluid shield.

2. The system of claim 1, wherein the pressurized fluid is water or air.

3. The system of claim 1, wherein the reservoir contains a disinfectant, the processing circuitry being further configured to instruct mixing of the disinfectant with the pressurized fluid pumped to the manifold.

4. The system of claim 1, wherein the bioaerosol particle entrainer is mixed with the pressurized fluid at a concentration of between 0.5% and 20%.

5. The system of claim 1, wherein the bioaerosol particle entrainer includes triethylene glycol particles.

6. The system of claim 5, wherein the triethylene glycol particles are between 1.26 μm and 3.72 μm.

7. The system of claim 1, wherein the manifold has a substantially-arced shape, the fluid stream directed therefrom forming a semi-cylindrical fluid column.

8. The system of claim 1, further comprising a vacuum, the processing circuitry being further configured to instruct the vacuum to evacuate the directed fluid stream from the dental operatory.

9. The system of claim 1, wherein the plurality of apertures have a diameter of between 3 mm and 6 mm.

10. A method for removing pathogens from a dental operatory, comprising:

pressurizing, with a fluid pump, a fluid within a fluid source, pumping, with the fluid pump, the pressurized fluid to a manifold in fluid connection with the fluid source, the manifold including a plurality of apertures for directing a fluid stream, mixing a particle entrainer disposed within a reservoir, with the pressurized fluid pumped to the fluid source, and directing, through the plurality of apertures, the pressurized fluid such that the directed fluid stream generates a fluid shield relative to an object, the particle entrainer being present within the fluid shield.

11. The method of claim 10, wherein the pressurized fluid is water or air.

12. The method of claim 10, wherein the reservoir contains a disinfectant, and the disinfectant is mixed with the pressurized fluid pumped to the manifold.

13. The method of claim 10, wherein the particle entrainer includes triethylene glycol particles.

14. The method of claim 13, wherein the triethylene glycol particles are between 1.26 μm and 3.72 μm.

15. The method of claim 10, wherein the manifold has a substantially-arced shape, the fluid stream directed therefrom forming a semi-cylindrical fluid column.

16. The method of claim 10, wherein the plurality of apertures have a diameter of between 3 mm and 6 mm.

17. A system for removing pathogens, comprising:

a manifold in fluid connection with a fluid source, the manifold including a plurality of apertures for directing a fluid stream, a reservoir containing at least a bioaerosol particle entrainer, a fluid pump for pressurizing a fluid within the fluid source, and processing circuitry configured to instruct the fluid pump to pressurize the fluid, instruct the fluid pump to pump the pressurized fluid to the manifold such that the directed fluid stream generates a fluid shield relative to an object, and instruct mixing of the bioaerosol particle entrainer with the pressurized fluid pumped to the manifold such that the bioaerosol particle entrainer is introduced into the fluid shield.

18. The system of claim 17, wherein the pressurized fluid is water or air.

19. The system of claim 17, wherein the reservoir contains a disinfectant, the processing circuitry being further configured to instruct mixing of the disinfectant with the pressurized fluid pumped to the manifold.

20. The system of claim 17, further comprising a vacuum, the processing circuitry being further configured to instruct the vacuum to evacuate the directed fluid stream.

* * * * *